US008921118B2

(12) United States Patent
Siegel et al.

(10) Patent No.: US 8,921,118 B2
(45) Date of Patent: Dec. 30, 2014

(54) PAPER-BASED MICROFLUIDIC SYSTEMS

(75) Inventors: Adam C. Siegel, Cambridge, MA (US); Scott T. Phillips, Cambridge, MA (US); Michael D. Dickey, Cambridge, MA (US); Dorota Rozkiewicz, Somerville, MA (US); Benjamin Wiley, Somerville, MA (US); George M. Whitesides, Newton, MA (US); Andres W. Martinez, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 795 days.

(21) Appl. No.: 12/934,857

(22) PCT Filed: Mar. 27, 2009

(86) PCT No.: PCT/US2009/038699

§ 371 (c)(1),
(2), (4) Date: Jan. 28, 2011

(87) PCT Pub. No.: WO2009/121041

PCT Pub. Date: Oct. 1, 2009

(65) Prior Publication Data

US 2011/0111517 A1 May 12, 2011

Related U.S. Application Data

(60) Provisional application No. 61/039,858, filed on Mar. 27, 2008, provisional application No. 61/039,958, filed on Mar. 27, 2008.

(51) Int. Cl.
*G01N 33/00* (2006.01)
*B01L 3/00* (2006.01)

(52) U.S. Cl.
CPC ..... *B01L 3/502707* (2013.01); *B01L 2300/025* (2013.01); *B01L 2300/161* (2013.01); *B01L 2200/027* (2013.01); *B01L 2300/12* (2013.01); *B01L 2200/10* (2013.01); *B01L 2200/16* (2013.01); *B01L 2200/0642* (2013.01); *B01L 2300/0809* (2013.01); *B01L 2200/12* (2013.01); *B01L 2300/087* (2013.01); *B01L 2300/0645* (2013.01); *B01L 2300/0819* (2013.01); *B01L 2300/0636* (2013.01); *B01L 2300/1827* (2013.01)
USPC ............ 436/164; 436/174; 436/180; 422/412

(58) Field of Classification Search
CPC .................... B01L 3/502707; B01L 2200/027; B01L 2200/0642; B01L 2200/10; B01L 2220/12; B01L 2200/16; B01L 2300/025; B01L 2300/0636; B01L 2300/0645; B01L 2300/0809; B01L 2300/0819; B01L 2300/087; B01L 2300/12; B01L 2300/161; B01L 2300/1827
See application file for complete search history.

(56) References Cited

U.S. PATENT DOCUMENTS 4,459,360 A 7/1984 Marinkovich
4,567,149 A 1/1986 Sell et al.

(Continued)

FOREIGN PATENT DOCUMENTS

EP 2143491 1/2010
JP 08233799 A 9/1996

(Continued)

OTHER PUBLICATIONS

Aikio, et al., "Bioactive Paper and Fibre Products: Patent and Literary Survey," VTT Working Papers 51, VTT-Work-51, 2006, 84 pages.

(Continued)

*Primary Examiner* — Christopher A Hixson
(74) *Attorney, Agent, or Firm* — Wilmer Cutler Pickering Hale and Dorr LLP

(57) ABSTRACT

Paper-based microfluidic systems and methods of making the same are described.

20 Claims, 12 Drawing Sheets

(56) References Cited

U.S. PATENT DOCUMENTS

| | | | | |
|---|---|---|---|---|
| 4,618,475 | A | 10/1986 | Wang | |
| 4,657,869 | A | 4/1987 | Richards et al. | |
| 4,668,564 | A | 5/1987 | Orchard | |
| 4,668,619 | A | 5/1987 | Greenquist et al. | |
| 4,743,530 | A | 5/1988 | Farid et al. | |
| 4,757,004 | A | 7/1988 | Houts et al. | |
| 4,861,711 | A | 8/1989 | Friesen et al. | |
| 4,981,653 | A | 1/1991 | Marino | |
| 5,120,544 | A | 6/1992 | Henley | |
| 5,122,452 | A | 6/1992 | Yamazaki et al. | |
| 5,169,757 | A | 12/1992 | Yamazaki et al. | |
| 5,209,904 | A | 5/1993 | Forney et al. | |
| 5,266,179 | A | 11/1993 | Nankai et al. | |
| 5,279,944 | A | 1/1994 | Fabrizi et al. | |
| 5,409,664 | A | 4/1995 | Allen | |
| 5,648,252 | A | 7/1997 | Dumitriu et al. | |
| 5,658,444 | A * | 8/1997 | Black et al. | 204/403.09 |
| 5,707,818 | A | 1/1998 | Chudzik et al. | |
| 5,834,226 | A | 11/1998 | Maupin | |
| 5,858,392 | A | 1/1999 | Dumitriu et al. | |
| 5,869,172 | A | 2/1999 | Caldwell | |
| 5,897,522 | A | 4/1999 | Nitzan | |
| 5,906,934 | A | 5/1999 | Grande et al. | |
| 5,925,259 | A | 7/1999 | Biebuyck et al. | |
| 5,941,862 | A | 8/1999 | Haynes et al. | |
| 6,004,442 | A | 12/1999 | Choulga et al. | |
| 6,025,203 | A | 2/2000 | Vetter et al. | |
| 6,060,534 | A | 5/2000 | Ronan et al. | |
| 6,180,239 | B1 | 1/2001 | Whitesides et al. | |
| 6,202,471 | B1 | 3/2001 | Yadav et al. | |
| 6,210,907 | B1 | 4/2001 | Cha | |
| 6,284,072 | B1 | 9/2001 | Ryan et al. | |
| 6,319,310 | B1 | 11/2001 | Wong et al. | |
| 6,391,523 | B1 | 5/2002 | Hurditch et al. | |
| 6,416,642 | B1 | 7/2002 | Alajoki et al. | |
| 6,440,645 | B1 | 8/2002 | Yon-Hin et al. | |
| 6,440,725 | B1 * | 8/2002 | Pourahmadi et al. | 435/288.5 |
| 6,478,938 | B1 | 11/2002 | Paek et al. | |
| 6,566,575 | B1 | 5/2003 | Stickels et al. | |
| 6,642,408 | B2 | 11/2003 | Batlaw et al. | |
| 6,713,309 | B1 | 3/2004 | Anderson et al. | |
| 6,761,962 | B2 | 7/2004 | Bentsen et al. | |
| 6,783,735 | B2 | 8/2004 | Vanmaele et al. | |
| 6,816,125 | B2 | 11/2004 | Kuhns et al. | |
| 6,844,200 | B2 | 1/2005 | Brock | |
| 6,877,892 | B2 | 4/2005 | Karp | |
| 6,880,576 | B2 | 4/2005 | Karp et al. | |
| 6,887,701 | B2 | 5/2005 | Anderson et al. | |
| 6,919,046 | B2 | 7/2005 | O'Connor et al. | |
| 6,931,523 | B1 | 8/2005 | Tomoson et al. | |
| 6,935,772 | B2 | 8/2005 | Karp et al. | |
| 6,951,682 | B1 | 10/2005 | Zebala | |
| 6,951,757 | B2 | 10/2005 | Sabatini | |
| 6,989,128 | B2 | 1/2006 | Alajoki et al. | |
| 7,008,799 | B1 | 3/2006 | Zimmer et al. | |
| 7,186,352 | B2 | 3/2007 | Morse et al. | |
| 7,291,857 | B2 | 11/2007 | Tanaka et al. | |
| 7,303,923 | B2 | 12/2007 | Hardman et al. | |
| 8,206,992 | B2 | 6/2012 | Reches et al. | |
| 8,377,710 | B2 | 2/2013 | Whitesides | |
| 2002/0006604 | A1 | 1/2002 | Schwabacher | |
| 2002/0106786 | A1 * | 8/2002 | Carvalho et al. | 435/287.3 |
| 2002/0187074 | A1 | 12/2002 | O'Connor et al. | |
| 2002/0187560 | A1 | 12/2002 | Pezzuto et al. | |
| 2003/0032203 | A1 | 2/2003 | Sabatini et al. | |
| 2003/0116552 | A1 | 6/2003 | Santoruvo et al. | |
| 2003/0148401 | A1 | 8/2003 | Agrawal et al. | |
| 2004/0067166 | A1 | 4/2004 | Karinka et al. | |
| 2004/0103808 | A1 | 6/2004 | Lochun et al. | |
| 2004/0119070 | A1 | 6/2004 | Roach et al. | |
| 2005/0136501 | A1 | 6/2005 | Kuriger | |
| 2005/0145496 | A1 | 7/2005 | Goodsaid et al. | |
| 2005/0169962 | A1 | 8/2005 | Bhatia et al. | |
| 2005/0196702 | A1 | 9/2005 | Bryant et al. | |
| 2005/0266582 | A1 | 12/2005 | Modlin et al. | |
| 2006/0014003 | A1 | 1/2006 | Libera et al. | |
| 2006/0038182 | A1 | 2/2006 | Rogers et al. | |
| 2006/0088857 | A1 | 4/2006 | Attiya et al. | |
| 2006/0130054 | A1 | 6/2006 | Bocking et al. | |
| 2006/0226575 | A1 | 10/2006 | Maghribi et al. | |
| 2007/0179117 | A1 | 8/2007 | Reiner et al. | |
| 2007/0196819 | A1 | 8/2007 | Asberg et al. | |
| 2007/0224701 | A1 | 9/2007 | Rosenstein | |
| 2007/0278097 | A1 | 12/2007 | Bhullar et al. | |
| 2007/0298433 | A1 | 12/2007 | Sia et al. | |
| 2009/0298191 | A1 | 12/2009 | Whitesides et al. | |
| 2010/0210029 | A1 * | 8/2010 | Meinhart et al. | 436/168 |
| 2011/0123398 | A1 | 5/2011 | Carrilho et al. | |
| 2011/0189786 | A1 | 8/2011 | Reches et al. | |
| 2012/0181184 | A1 | 7/2012 | Whitesides et al. | |
| 2012/0198684 | A1 | 8/2012 | Carrilho et al. | |

FOREIGN PATENT DOCUMENTS

| | | | |
|---|---|---|---|
| WO | WO-97/48257 | | 12/1997 |
| WO | WO-99/46644 | | 9/1999 |
| WO | WO-00/33078 | | 6/2000 |
| WO | WO-01/02093 | A2 | 1/2001 |
| WO | WO-01/25138 | | 4/2001 |
| WO | WO-0224322 | A2 | 3/2002 |
| WO | WO-03/015890 | A1 | 2/2003 |
| WO | WO-2004/006291 | A2 | 1/2004 |
| WO | WO-2004/080138 | | 9/2004 |
| WO | WO-2005/090975 | A1 | 9/2005 |
| WO | WO-2005/090983 | A2 | 9/2005 |
| WO | WO-2005/107938 | | 11/2005 |
| WO | WO-2005/109005 | A1 | 11/2005 |
| WO | WO-2006/018044 | | 2/2006 |
| WO | WO-2006/076703 | | 7/2006 |
| WO | WO-2006120221 | A1 | 11/2006 |
| WO | WO-2007/029250 | | 3/2007 |
| WO | WO-2007081848 | | 7/2007 |
| WO | WO-2007/116056 | | 10/2007 |
| WO | WO-2008/049083 | | 4/2008 |
| WO | WO-2009/120963 | | 10/2009 |
| WO | WO-2009/121037 | A2 | 10/2009 |
| WO | WO-2009/121038 | | 10/2009 |
| WO | WO-2009/121041 | A2 | 10/2009 |
| WO | WO-2009/121043 | A2 | 10/2009 |
| WO | WO-2010/022324 | | 2/2010 |
| WO | WO-2010/102279 | A1 | 9/2010 |
| WO | WO-2010/102294 | A1 | 9/2010 |
| WO | WO-2011/097412 | | 8/2011 |

OTHER PUBLICATIONS

Author Unknown, "Focus: Lab on Paper, DOI: 10.1039/b814043j," Lab Chip, vol. 8, No. 12, Dec. 2008, pp. 1988-1991, XP002585318, The Royal Society of Chemistry.

Berggren, et al., "Paper Electronics and Electronic Paper," IEEE, Section 12: Flexible Systems, 2001, pp. 300-303.

Bracher, et al., "Heterogeneous Films of Ionotropic Hydrogels Fabricated from Delivery Templates of Patterned Paper," Adv. Mater., 2008, pp. 1807-1812.

Brooks, et al., "A Simple Artificial Urine for the Growth of Urinary Pathogens," Lett. Appl. Microbiol., 1997, 24, pp. 203-206.

Bruzewicz, et al., "Low-Cost Printing of Poly(dimethylsiloxane) Barriers to Define Microchannels in Paper," Anal. Chem., 2008, 80, pp. 3387-3392.

Bruzewicz, et al., "Paper: Fabrication of a Modular Tissue Construct in a Microfluidic Chip," Lab Chip, 2008, 8, pp. 663-671.

Campana, et al., "Double and Triple Staining Methods for Studying the Proliferative Activity of Human B and T Lymphoid Cells," Journal of Immunological Methods, 107, 1988, pp. 79-88.

Carrilho, et al., "Paper Microzone Plates," Analytical Chemistry, vol. 81, No. 15, Aug. 2009, pp. 5990-5998.

Carrilho, et al., "Understanding Wax Printing: A Simple Micropatterning Process for Paper-Based Microfluidics," Analytical Chemistry, vol. 81, No. 16, Aug. 2009, pp. 7091-7095.

(56) References Cited

OTHER PUBLICATIONS

Chadee, et al., "Increased Phosphorylation of Histone H1 in Mouse Fibroblasts Transformed with Oncogenes or Constitutively Active Mitogen-Activated Protein Kinase Kinase," The Journal of Biological Chemistry, vol. 270, No. 34, Aug. 1995, pp. 20098-20105.
Cheng, et al., "Clinical Analytics: Paper-Based ELISA**," Agnew. Chem., 2010, 122, pp. 1-5.
Chin, et al., "Lab-on-a-chip Devices for Global Health: Past Studies and Future Opportunities," Lab Chip, 2007, 7, pp. 41-57, A Journal of the Royal Society of Chemistry.
Costerton, et al., "Bacterial Biofilms: a Common Cause of Persistent Infections," Science Mag., 1999, pp. 1318-1322.
Daar, et al., "Top Ten Biotechnologies for Improving Health in Developing Countries," Nature Genetics, vol. 32, Oct. 2002, pp. 229-232.
Donlan, "Biofilm Formation: A Clinically Relevant Microbiological Process," Healthcare Epidemiology, CID 2001:33, Oct. 2001, pp. 1387-1392.
Donlan, et al., "Biofilm Formation on Cast Iron Substrata in Water Distribution Systems," Wat. Res. vol. 28, No. 6, pp. 1497-1503, 1994.
Donlan, et al., "Reviews: Biofilms: Survival Mechanisms of Clinically Relevant Microorganisms," Clinical Microbiology Reviews, vol. 15, No. 2, Apr. 2002, pp. 167-193.
Dungchai, et al., "Electrochemical Detection for Paper-Based Microfluidics," Anal. Chem., 2009, 81, pp. 5821-5826.
Ebeling, "The Permanent Life of Connective Tissue Outside of the Organism," J. Exp. Med., 17, 1913, 15 pages.
Harrison, et al., "Methodology Article: High-Throughput Metal Susceptibility Testing of Microbial Biofilms," BMC Microbiology, 2005, 5:53, 11 pages.
International Search Report and Written Opinion of the International Searching Authority, the European Patent Office, for International Application No. PCT/US2007/081848, dated Jan. 28, 2009, 12 pages.
International Search Report and Written Opinion of the International Searching Authority, the European Patent Office, for PCT/US2010/026499, dated Jun. 16, 2010, 2 pages.
International Search Report and Written Opinion of the International Searching Authority, the Korean Intellectual Property Office, for International Application No. PCT/US2009/038566, dated Dec. 16, 2009, 10 pages.
International Search Report and Written Opinion of the International Searching Authority, the Korean Intellectual Property Office, for International Application No. PCT/US2009/038694 dated Nov. 12, 2009, 10 pages.
International Search Report and Written Opinion of the International Searching Authority, the Korean Intellectual Property Office, for PCT/US2009/038693, dated Oct. 28, 2009, 8 pages.
International Search Report and Written Opinion of the International Searching Authority, the Korean Intellectual Property Office, for PCT/US2009/038699, dated Oct. 28, 2009, 9 pages.
International Search Report and Written Opinion of the International Searching Authority, the Korean Intellectual Property Office, for PCT/US2009/038702, dated Nov. 11, 2009, 7 pages.
International Search Report of the International Searching Authority, the European Patent Office, for PCT/US2010/026547, dated Jul. 19, 2010, 3 pages.
International Search Report of the International Searching Authority, the Korean Intellectual Property Office, for PCT/US2009/054601, dated Mar. 22, 2010, 2 pages.
Klajn, et al., "Multicolour Micropatterning of Thin Films and Dry Gels," Nature Materials, vol. 3, Oct. 2004, pp. 729-735.
Lahav, et al., "DO1: 10.1002/adma.200601843—Patterning of Poly(acrylic acid) by Ionic Exchange Reactions in Microfluidic Channels** ," Advanced Materials, 2006, 18, pp. 3174-3178.
Leary, et al., "Rapid and Sensitive Colorimetric Method for Visualizing Biotin-Labeled DNA Probes Hybridized to DNA or RNA Immobilized on Nitrocellulose: Bio-Blots," PNAS, vol. 80, No. 13, 1983, pp. 4045-4049.
Li, et al., "Thread as a Versatile Material for Low-Cost Microfluidic Diagnostics," Applied Materials & Interfaces, vol. 2, No. 1, Jan. 2010, 6 pages.
Liu, et al., "Three-Dimensional Photopatteming of Hydrogels Containing Living Cells," Biomed. Microdevices, 2002, 4, pp. 257-266.
Lu, et al., "Short Communication: Rapid Prototyping of Paper-Based Microfluidics with Wax for Low-Cost, Portable Bioassay," Electrophoresis, 2009, 30, pp. 1497-1500.
Mabey, et al., "Diagnostics for the Developing World," Nature Reviews / Microbiology, vol. 2, Mar. 2004, pp. 231-240.
Martinez, et al., "Diagnostics for the Developing World: Microfluidic Paper-Based Analytical Devices," Analytical Chemistry, vol. 82, No. 1, Jan. 2010, pp. 3-10.
Martinez, et al., "FLASH: A Rapid Method for Prototyping Paper-Based Microfluidic Devices," Lab Chip, 2008, 8, pp. 2146-2150, A Journal of the Royal Society of Chemistry.
Martinez, et al., "Paper: Programmable Diagnostic Devices Made from Paper and Tape," Lab Chip, Jul. 2010, 6 pages.
Martinez, et al., "Patterned Paper as a Platform for Inexpensive, Low-Volume, Portable Bioassays**," Agnew. Chem. Int. Ed., 2007, 46, pp. 1318-1320.
Martinez, et al., "Simple Telemedicine for Developing Regions: Camera Phones and Paper-Based Microfluidic Devices for Real-Time, Off-Site Diagnosis," Analytical Chemistry, vol. 80, No. 10, May 2008, pp. 3699-3707.
Martinez, et al., "Three-Dimensional Microfluidic Devices Fabricated in Layered Paper and Tape," PNAS, vol. 105, No. 50, Dec. 2008, pp. 19606-19611.
Matsumoto, et al., "Three-Dimensional Cell and Tissue Patterning in a Strained Fibrin Gel System," PLoS One, Nov. 2007, Issue No. 11, 6 pages.
Nelson, et al., "Three-Dimensional Lithographically Defined Organotypic Tissue Arrays for Quantitative Analysis of Morphogenesis and Neoplastic Progression," Nature Protocols, vol. 3, No. 4, 2008, pp. 674-678.
Nie et al., "Paper: Integration of Paper-based Microfluidic Devices with Commercial Electrochemical Readers," Lab Chip, Oct. 2010, 7 pages.
Peele, et al., "Semi-Automated vs. Visual Reading of Urinalysis Dipsticks," Clin. Chem, 1977, 23, pp. 2242-2246.
Pugia, et al., "High-Sensitivity Dye Binding Assay for Albumin in Urine," J. Clin. Lab. Anal. 1999, 13, pp. 180-187.
Reches, et al., "Thread as a Matrix for Biomedical Assays," Applied Materials & Interfaces, vol. xxx, No. xx, 000, xxxx, pp. A-G, 2010.
Shaw, et al., "Negative Photoresists for Optical Lithography," IBM Journal of Research and Development, vol. 41, No. 1/2, Jan./Mar. 1997, pp. 81-94, 15 pages.
Shimizu, et al., "Biofilm Formation on Hydrophilic Intraocular Lens Material," Current Eye Research, 31, 2006, pp. 989-997.
Sia, et al., "Microfluidic Devices Fabricated in Poly(dimethylsiloxane) for Biological Studies," Electrophoresis, 2003, 24, pp. 3563-3576.
Siegel, et al., "Foldable Printed Circuit Boards on Paper Substrates," Advanced Functional Materials, 2010, 20, pp. 28-35.
Smith, S.K., "Angiogenesis, Vascular Endothelial Growth Factor and the Endometrium," Hum. Reprod. Update 1998, 4, pp. 509-519.
Tang, et al., "Molding of Three-Dimensional Microstructures of Geis," J. Am. Chem. Soc., 2003, 125, pp. 12988-12989.
Urbich, et al., "Endothelial Progenitor Cells: Characterization and Role in Vascular Biology," Circulation Research, DOI: 10.1161/01.RES.0000137877.89448.78, Aug. 2004, pp. 343-353.
von Lode, P., "Point-of-care Immunotesting: Approaching the Analytical Performance of Central Laboratory Methods," Clinical Biochemistry, 38, 2005, pp. 591-606.
Washburn, E. W., "The Dynamics of Capillary Flow," The Physical Review, vol. XVII, No. 3, Second Series, Mar. 1921, pp. 273-283.
Winkleman, et al., "Patterning micron-sized features in a cross-linked poly (acrylic acid) film by a wet etching process," The Royal Society of Chemistry, 2007, pp. 108-116.
Xerox Corporation, "Material Safety Data Sheet for Xerox Phaser 6250 Color Laser Toner," 2003, pp. E-1-E-5, retrieved from http://www.office.xerox.com/userdoc/P6250/6250_Web/pdfs/msds.pdf.

(56) References Cited

OTHER PUBLICATIONS

Zhi, et al., "Multianalyte Immunoassay with Self-Assembled Addressable Microparticle Array on a Chip," Analytical Biochemistry, vol. 318, No. 2, Jul. 2003, pp. 236-243.

Zhu, et al., "Research Article: Proposal to Create Subspecies of *Rickettsia conorii* Based on Multi-Locus Sequence Typing and an Emended Description of *Rickettsia conorii*," BMC Microbiology, 2005, 5:11, 11 pages.

Muller et al., "Automatic Paper Chromatography," Analytical Chemistry, vol. 21, No. 9, Sep. 1949, pp. 1123-1125.

"Zone Quick from FCI Ophthalmics, Phenol Red Thread (PRT) Tear Test," retreived from www.fci-ophthalmics.com, author unknown, no. month listed, 1998, 1 page.

* cited by examiner

FIG. 9A
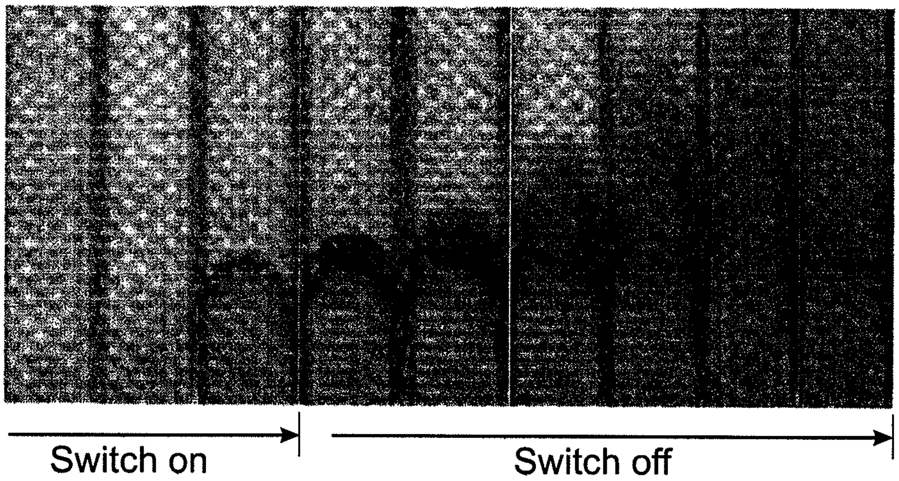
FIG. 9B
FIG. 9C
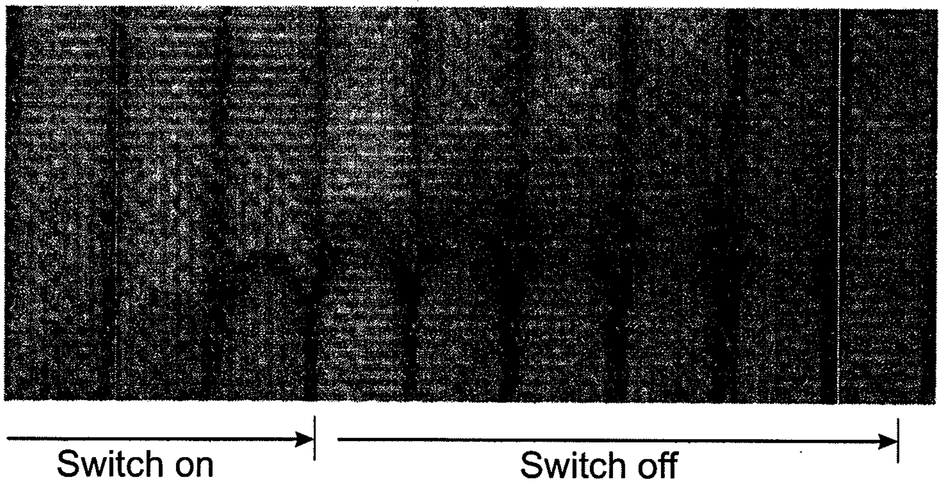
FIG. 9D

PAPER-BASED MICROFLUIDIC SYSTEMS

CROSS-REFERENCE TO RELATED APPLICATIONS

This application is a national stage of International (PCT) Patent Application Serial No. PCT/US2009/038699, filed Mar. 27, 2009, and published under PCT Article 21(2) in English, which claims the benefit of U.S. Provisional Application No. 61/039,858, filed Mar. 27, 2008, and U.S. Provisional Application No. 61/039,958, filed Mar. 27, 2008, the contents of the aforementioned provisional patent applications are hereby incorporated in their entirety herein.

BACKGROUND OF THE INVENTION

Most current bioanalytical assays are inaccessible for developing economies. Current diagnostic assays typically require large and expensive laboratory instruments that are operated by trained personnel. Thus, there remains a need for low-cost diagnostic assays that are not cumbersome and that can be performed on small sample volumes. Further, there remains a need for low-cost systems to detect trace levels of analytes in fluids for, e.g., (i) human health; (ii) illicit drug use; (iii) military and homeland security settings; and (iv) chemical pollution in the environment.

SUMMARY OF THE INVENTION

In one aspect, the invention features an assay device. The assay device comprises a porous, hydrophilic substrate; a fluid-impermeable barrier defining a boundary of an assay region and a boundary of a main channel region, the main channel region fluidically connected to the assay region; and a strip of conductive material disposed on the porous, hydrophilic substrate. In some embodiments, the porous, hydrophilic substrate comprises nitrocellulose acetate, cellulose acetate, cellulosic paper, filter paper, tissue paper, writing paper, paper towel, cloth, or porous polymer film.

In some embodiments, the fluid-impermeable barrier permeates the thickness of the porous, hydrophilic substrate.

In some embodiments, the strip of conductive material is disposed on one face of the substrate. In some embodiments, the strip conductive material is disposed on both faces of the substrate. In particular embodiments, the strip is positioned to span across the main channel region.

In some embodiments, the conductive material is a metal or a conductive polymer. In some embodiments, the conductive material is a metal. In particular embodiments, the metal is Sn, Zn, Au, Ag, Ni, Pt, Pd, Al, In, or Cu.

In some embodiments, the assay device further comprises an insulating material disposed between the conductive material and the porous, hydrophilic substrate. In some embodiments, the insulating material is tape, polysterene, polyethylene, or polyvinylchloride.

In particular embodiments, the main channel region comprises a sample deposition region, the main channel region providing a fluidic pathway within the porous, hydrophilic substrate between the sample deposition region and the assay region.

In some embodiments, the barrier further defines a plurality of assay regions and a plurality of main channel regions, the strip of conductive material spanning two or more channels.

In yet other embodiments, the assay region comprises a detection reagent. In some embodiments, the detection reagent is covalently bonded to the porous, hydrophilic substrate in the assay region. In other embodiments, the detection reagent is not covalently bonded to the porous, hydrophilic substrate in the assay region.

In some embodiments, the barrier comprises photoresist or a curable polymer. In particular embodiments, the barrier comprises SU-8 photoresist.

In some embodiments, the barrier has at least one dimension between about 100 μm and about 5 cm, between about 100 μm and about 1 cm, between about 100 μm and about 1 mm, or between about 100 μm and about 200 μm. In some embodiments, the main channel region has at least one lateral dimension between about 100 μm and about 5 cm, between about 100 μm and about 1 cm, between about 100 μm and about 1 mm, or between about 100 μm and about 200 μm. In some embodiments, the layer of conductive material has at least one lateral dimension between about 100 μm and about 5 cm, between about 100 μm and about 1 cm, between about 100 μm and about 1 mm, or between about 100 μm and about 200 μm.

In some embodiments, the conductive material has a resistance of about 10Ω to about 500Ω, about 20Ω to about 100Ω, or about 20Ω to about 50Ω.

In another aspect, the invention features an assay device. The assay device comprises a porous, hydrophilic substrate; a fluid-impermeable barrier defining (i) a boundary of a main channel region, (ii) boundaries of a first minor channel region and a second minor channel region, and (iii) boundaries of a first assay region and a second assay region, the first and second minor channel regions providing a fluidic pathway within the porous, hydrophilic substrate between the main channel region and a corresponding assay region; and a strip of conductive material disposed on the porous, hydrophilic substrate. In some embodiments, the porous, hydrophilic substrate comprises nitrocellulose acetate, cellulose acetate, cellulosic paper, filter paper, tissue paper, writing paper, paper towel, cloth, or porous polymer film.

In some embodiments, the fluid-impermeable barrier permeates the thickness of the porous, hydrophilic substrate In some embodiments, the strip of conductive material is disposed on one face of the substrate. In some embodiments, the strip of conductive material is disposed on both faces of the substrate.

In some embodiments, the assay device comprises a second strip of conductive material. In some embodiments, the second strip of conductive material is disposed on both faces of the substrate. In some embodiments, the first and second strips of conductive material are disposed on the same face or faces of the substrate. In some embodiments, the first and second strips of conductive material are disposed on opposite faces of the substrate.

In particular embodiments, the second strip of conductive material is positioned to span across the second minor channel region. In some embodiments, the first strip of conductive material does not span the second minor channel region. In some embodiments, the second strip of conductive material does not span the first minor channel region.

In other embodiments, the assay device comprises one or more additional minor channel regions and one or more additional assay regions, each minor channel region providing a fluidic pathway between the main channel region and a corresponding assay region.

In some embodiments, the conductive material is a metal or a conductive polymer. In some embodiments, the conductive material is a metal. In particular embodiments, the metal is Sn, Zn, Au, Ag, Ni, Pt, Pd, Al, In, or Cu.

In some embodiments, the assay device further comprises an insulating material disposed between the conductive material and the porous, hydrophilic substrate. In some embodiments, the insulating material is tape, polysterene, polyethylene, or polyvinylchloride.

In particular embodiments, the main channel region comprises a sample deposition region, the main channel region providing a fluidic pathway within the porous, hydrophilic substrate between the sample deposition region and the first minor channel region and the second minor channel region.

In yet other embodiments, the assay regions comprise a detection reagent. In some embodiments, the detection reagent is covalently bonded to the porous, hydrophilic substrate in the assay region. In other embodiments, the detection reagent is not covalently bonded to the porous, hydrophilic substrate in the assay region.

In some embodiments, the barrier comprises photoresist or a curable polymer. In particular embodiments, the barrier comprises SU-8 photoresist.

In some embodiments, the barrier has at least one dimension between about 100 μm and about 5 cm, between about 100 μm and about 1 cm, between about 100 μm and about 1 mm, or between about 100 μm and about 200 μm. In some embodiments, the main channel region has at least one lateral dimension between about 100 μm and about 5 cm, between about 100 μm and about 1 cm, between about 100 μm and about 1 mm, or between about 100 μm and about 200 μm. In some embodiments, the layer of conductive material has at least one lateral dimension between about 100 μm and about 5 cm, between about 100 μm and about 1 cm, between about 100 μm and about 1 mm, or between about 100 μm and about 200 μm.

In some embodiments, the conductive material has a resistance of about 10Ω to about 500Ω, about 20Ω to about 100Ω, or about 20Ω to about 50Ω.

In another aspect, the invention features a method of controlling the movement of a fluid sample through an assay device, e.g., an assay device described herein. The method comprises applying an electric current to the conductive material on the assay device; and contacting the main channel region with a fluid sample, wherein applying the electric current to the conductive material prevents the fluidic flow of the sample from the main channel region to the assay region. In some embodiments, applying the electric current evaporates at least a portion of the fluid sample and concentrates an analyte at the boundary of the main channel and the portion of the conductive material disposed across the main channel region.

In some embodiments, the method further comprises removing the electric current. In particular embodiments, removing the electric current allows the fluidic flow of the sample from the main channel to the assay region.

In another aspect, the invention features a method of controlling the movement of a fluid sample through an assay device, e.g., an assay device described herein and comprising at least two strips of conductive material, each spanning a first and second minor channel region, respectively. The method comprises applying an electric current to a first strip of conductive material; and contacting the main channel region with a fluid sample, wherein applying the electric current to the first strip of conductive material prevents the fluidic flow of the sample from a first minor channel region to a first assay region.

In some embodiments, applying the electric current evaporates at least a portion of the fluid sample and concentrates an analyte at the boundary of the first minor channel and the first strip of conductive material.

In other embodiments, the method further comprises applying an electric charge to a second strip of conductive material, wherein applying the electric current to the second strip of conductive material prevents the fluidic flow of the sample from a second minor channel region to a second assay region.

In some embodiments, the electric current to the strips of conductive material is turned on or off, allowing or impeding the flow of the fluid sample through the corresponding minor channel regions and into corresponding assay regions.

In another aspect, the invention features a microfluidic device. The microfluidic device comprises a porous, hydrophilic substrate; a fluid-impermeable barrier, the barrier permeating the thickness of the porous, hydrophilic substrate and defining within the porous, hydrophilic substrate a boundary of an open-ended channel having first and second lateral walls; and an electrically conductive pathway disposed on the porous, hydrophilic substrate, the electrically conductive pathway comprising (i) a strip of conductive material forming an open circuit in the absence of an electrically conductive material bridging the first and second lateral walls; and (ii) a battery, an electrically-responsive indicator, and a resistor electrically connected to the strip of conductive material.

In another aspect, the invention features a method of detecting the presence of high electrolyte concentration in a fluid sample. The method comprises providing the microfluidic device described herein; and contacting the open-ended channel with a fluid sample, wherein the fluid sample flows through the channel and bridges the two lateral walls of the channel, completing the electrically conductive pathway, wherein a detectable signal produced by the electrically-responsive indicator upon the completion of the electrically conductive pathway is indicative of a high electrolyte concentration in the fluid.

BRIEF DESCRIPTION OF THE DRAWINGS

The foregoing and other objects of the present invention, the various features thereof, as well as the invention itself, may be more fully understood from the following description, when read together with the accompanying drawings, in which:

FIG. 8A depicts a device that has the right switch turned on and the left switch turned off. FIG. 8B depicts a device that has the right switch turned on and the left switch turned off. FIG. 8C and FIG. 8D depict one device; with either the right switch on (FIG. 8C), or the right switch off (FIG. 8D).

FIG. 9 is a series of representations of photographs of a multiple-channel microfluidic device with a wire crossing 8 of 16 channels. FIG. 9A depicts sequential images of the flow and control of solution of blue dye using curved wire. FIG. 9B depicts an enlargement of one channel with wire. FIG. 9C depicts the same device subsequently used to control the flow of yellow dye. FIG. 9D depicts an enlargement of one channel with wire.

FIG. 10 is a series of representations of photographs of a multiple-channel microfluidic device with switches.

DETAILED DESCRIPTION

Figure 1A:
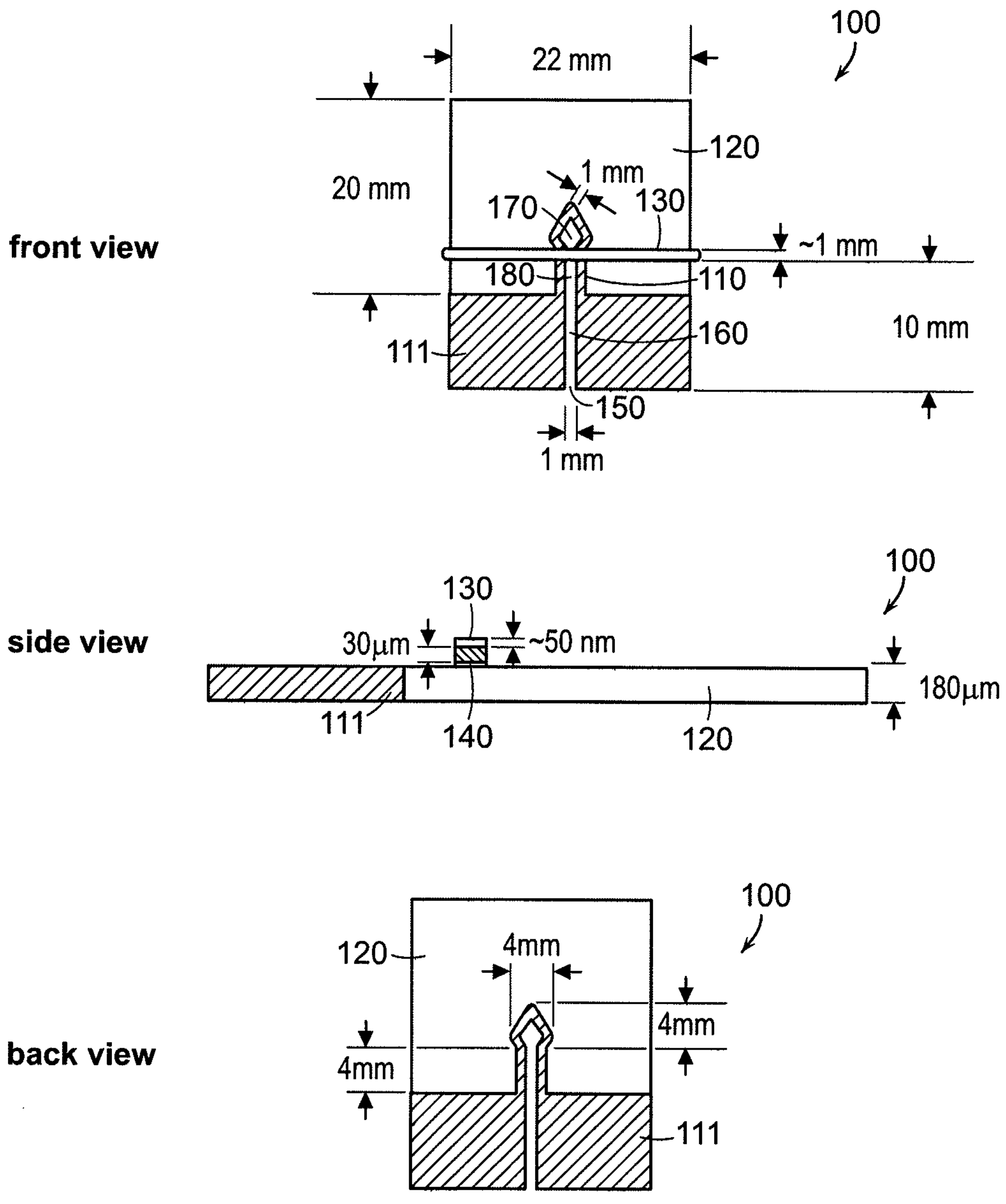
FIG. 1A is a schematic illustration of a paper-based microfluidic system having a single detection zone.

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

General

Under some aspects, porous, hydrophilic substrates are patterned with hydrophobic barriers to provide a class of low-cost, portable, and technically simple platforms for running multiplexed bioassays on biological liquids. One example of a useful hydrophilic substrate for assays is paper, which is inexpensive, readily commercially available, disposable, wicks liquids quickly, and does not need careful handling as do some conventional platforms. The paper or other porous, hydrophilic substrate is patterned with hydrophobic barriers that provide spatial control of biological fluids and enable fluid transport due to capillary action within the regions the barriers define. The hydrophobic barriers can be polymeric, for example a curable polymer or a photoresist, and provide a substantially impermeable barrier throughout the thickness of the porous, hydrophilic substrate within defined areas.

The paper or other porous, hydrophilic substrate also includes a layer of conductive material, e.g., metal, affixed to one side of the substrate. The conductive material can be used to control the flow of a fluid sample through the substrate, e.g., to concentrate analytes in fluids and for detecting trace levels of multiple analytes in a sample, or to create "switches" and "valves" to control the flow of fluid samples into different regions of a bioassay. The switches and valves are compatible with two-dimensional (2-D), lateral-flow paper-based microfluidic devices as well as three-dimensional (3-D), flow-through devices (which consist of alternating layers of paper and tape stacked on top of one another). The combination of switches and valves leads to simple, inexpensive, and paper-based microfluidic devices that control the movement of fluids precisely without the added complication of pumps or other external equipment for function.

In some embodiments, an insulating material layer is disposed between a conductive material and a porous, hydrophilic substrate. Non-limiting examples of insulating material that can be used include tape, polysterene, polyethylene, polyvinylchloride, thin film photoresist, polyimide, glues, epoxies, wax, PDMS, silicone, latex, or any other suitable insulating polymers, or any combination thereof. In some embodiments, a conductive material is attached to an insulating material layer to form a composite sheet (e.g., an insulated conductive layer).

Assay Devices

FIG. 1A is a schematic illustration of an assay device having a hydrophilic substrate, hydrophobic barriers, and conductive materials according to some embodiments of the invention. The device 100 includes a patterned hydrophobic barrier 110, e.g., SU-8 photoresist, porous, hydrophilic substrate 120, e.g., chromatography paper, a conductive material 130, e.g., metal, and insulating layer 140, e.g., tape. The hydrophobic barrier 110 defines regions in the substrate 120 that can be used to perform bioassays. In the illustrated embodiment, barrier 110 defines a sample deposition region 150, where a fluid sample can be deposited, assay region 170, and main channel region 160, which wicks the fluid sample by capillary action from deposition region 150 to assay region 170.

When electric current is applied to conductive material 130, the conductive material 130 becomes warm and this heat is transferred through insulating layer 140 and into main channel region 160. Since the conducting material 130 and insulating layer 140 are placed on one side of device 100, the fluid in main channel region 160 can evaporate from the back side of device 100. Thus, when electric current is applied to conductive material 130, the fluid sample wicks through main channel region 160 to region 180, where conductive material 130 contacts hydrophobic barrier 110, and does not flow to assay region 170.

Figure 3A:
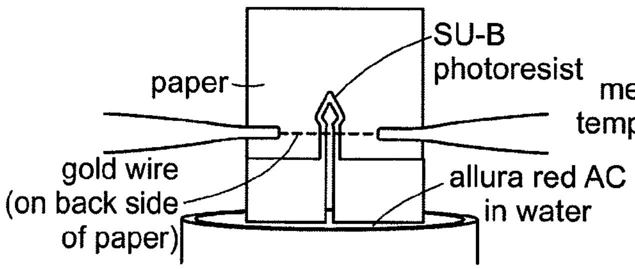
FIG. 3A is a representation of a photograph of a μ-PAD connected to a tunable current source.
Figure 3B:
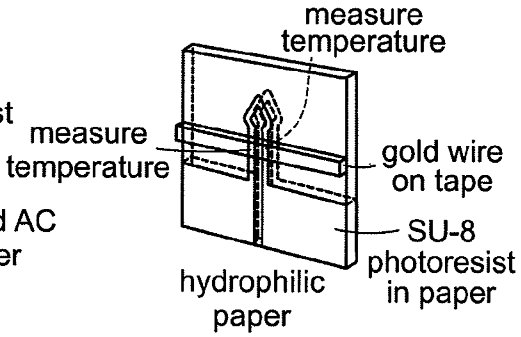
FIG. 3B is a schematic of a μ-PAD depicting locations on the device where temperature was measured using an IR thermometer.
Figure 3C:
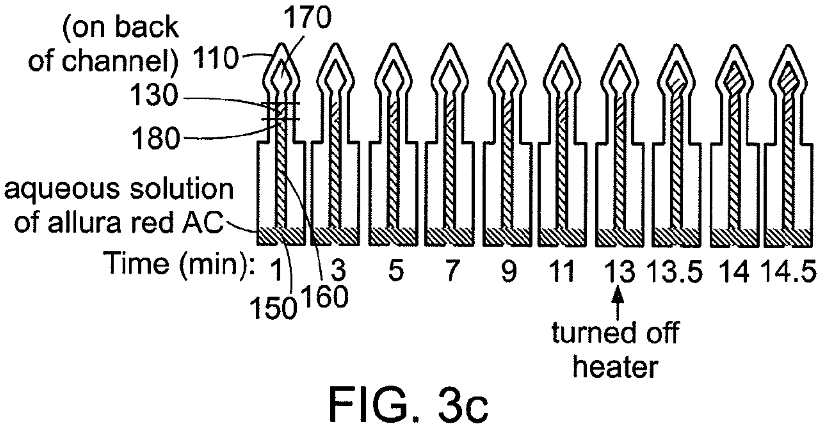
FIG. 3C is a series of representations of photographs depicting a time course of a heated μ-PAD dipped into 165 μM allura red AC.

FIG. 3C is a series of images depicting the flow of an aqueous solution of allura red AC through the assay device 100 of FIG. 1A with and without electric current being applied to conductive material. The solution flowed from sample deposition region 150 through main channel region 160 to region 180, at the region that conducting material 130 contacts hydrophobic barrier 110. The fluid sample did not flow to assay region 170. The amount of dye continued to accumulate at region 180 for 13 minutes, as the fluid evaporated at region 180. At 13 minutes, the electric current to conductive material 130 was turned off. By 13.5 minutes, the fluid sample began to flow into assay region 170. As described in greater detail below, assay region 170 can be treated with a detection reagent to detect the presence of a particular analyte within the fluid sample.

Figure 1B:
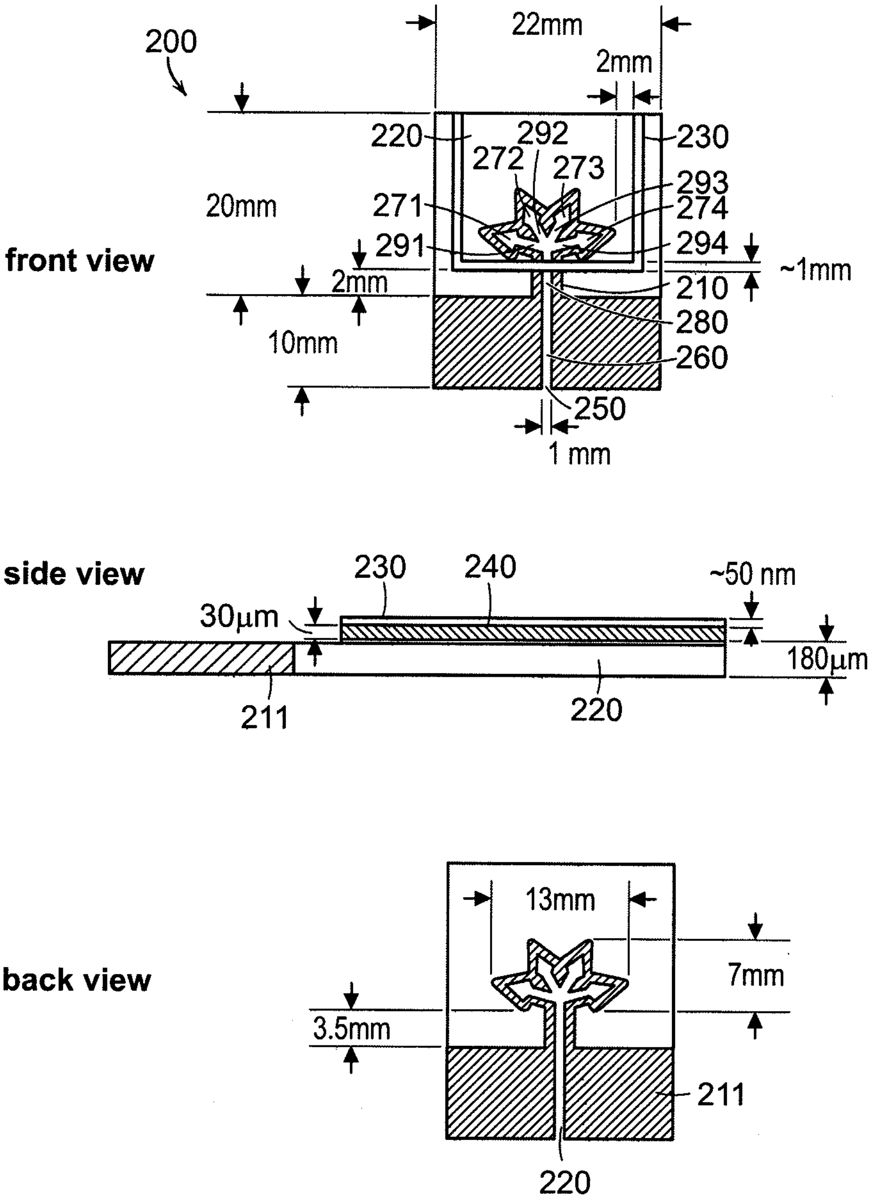
FIG. 1B is a schematic illustration of a paper-based microfluidic system having four detection zones.

FIG. 1B is a schematic illustration of an assay device 200 having patterned hydrophobic barrier 210, e.g., SU-8 photoresist, porous, hydrophilic substrate 220, e.g., chromatography paper, a conductive material 230, e.g., metal, and insulating layer 240, e.g., tape. The hydrophobic barrier 210 defines a sample deposition region 250, where a fluid sample can be deposited, assay regions 271, 272, 273, 274, minor channel regions 291, 292, 293, 294, and main channel region 260, which wicks the fluid sample by capillary action from deposition region 250 to assay regions 271, 272, 273, and 274 through minor channel regions 291, 292, 293, and 294, respectively. When electric current is applied to conductive material 230, the fluid sample wicks through main channel region 260 to region 280, where conductive material 230 contacts hydrophobic barrier 210, and does not flow to minor channel regions 291, 292, 293, or 294. Assays regions 271, 272, 273, and 274 can be treated with detection reagents, e.g., the same or different detection reagents, to detect the presence of particular analytes within the fluid sample.

In device 200 depicted in FIG. 1B, assay regions 271, 272, 273, and 274 are spaced equally from main channel region 260 (about 2 mm from main channel region 260). In this embodiment, assay regions 271, 272, 273, and 274 receive equal volumes of fluid sample, and assay regions 271, 272, 273, and 274 fill at a similar rate.

In the devices illustrated in FIGS. 1A and 1B, main channel region is 1 mm wide. In other embodiments, main channel region is narrower, e.g., around 100 μm, to accommodate for small fluid sample volumes (e.g., less than about 3 μL). The devices in FIG. 1A and FIG. 1B also include a region 111, or 211 of paper embedded with SU-8 photoresist, which can prevent fluids from entering the device adventitiously.

Figure 7:
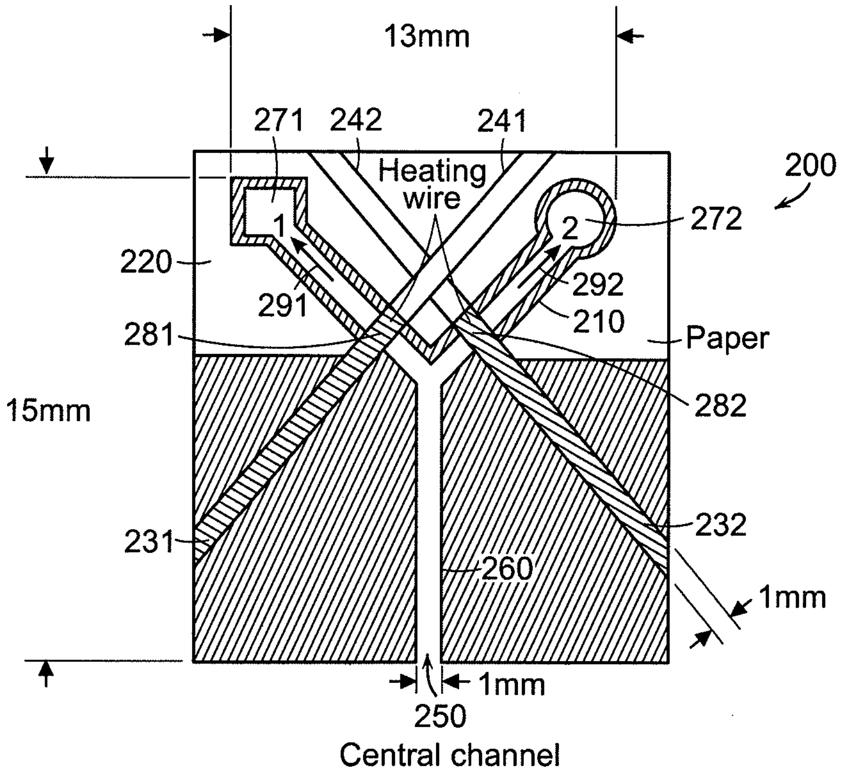
FIG. 7 is a schematic drawing of the device.

FIG. 7 is a schematic illustration of an assay device having a hydrophilic substrate, a hydrophobic barrier, and two layers of conductive materials. The device 200 includes a patterned hydrophobic barrier 210, e.g., SU-8 photoresist, porous, hydrophilic substrate 220, e.g., chromatography paper, conductive material layers 231 and 232, and insulating layers 241 and 242. The hydrophobic barrier 210 defines a sample deposition region 250, where a fluid sample can be deposited, assay regions 271 and 272, minor channel regions 291 and 292, and main channel region 260, which wicks the fluid sample by capillary action from deposition region 250 to assay regions 271 and 272 through minor channel regions 291 and 292, respectively. Assays regions 271 and 272 can be treated with detection reagents, e.g., the same or different detection reagents, to detect the presence of particular analytes within the fluid sample.

When electric current is applied to conductive material layer 231, conductive material layer 231 becomes warm and this heat is transferred through insulating layer 241 and into minor channel region 291. Since the conducting material layer 231 and insulating layer 241 are placed on one side of device 200, the fluid in minor channel region 291 can evaporate from the back side of device 200. Thus, when electric current is applied to conductive material layer 231, the fluid sample wicks through main channel region 260 to minor channel region 291 to region 281, where conductive material layer 231 contacts hydrophobic barrier 210, and does not flow to assay region 271. When electric current is applied to conductive material layer 231, the fluid sample flows from main channel region 260 to assay region 272 through minor channel region 292.

When conductive material layers 231 and 232 are about 60-70° C., the movement of fluid is stopped (is switched off), and when the temperature of conductive material layers 231 and 232 is below 60° C., the movement of fluid is modulated (creating valves). The time required to turn on and off the switches and valves (i.e., the time for conductive material layers 231 and 232 to heat and cool) is less than 1 s at 0.2 volts, but can be adjusted by applying different levels of current. Both components can be turned on and off many times.

FIGS. 8A and 8B are images depicting the flow of an aqueous solution of red dye through the assay device 200 of FIG. 7. Conductive material layers 231 and 232 were 1 mm-wide×50 nm-thick gold conductive pathways deposited onto one side of insulating layers (30 μm-thick). As depicted in FIG. 8A, when electric current was applied to conductive material layer 232, the fluid sample flowed from main channel region 260 to assay region 271. However, the fluid sample did not flow to assay region 272, but was stopped at region 282. As shown in FIG. 8B, when the electric current to conductive material layer 232 was turned off and an electric current was applied to conductive material layer 231, the fluid sample flowed from main channel region 260 to assay region 272 and stopped flowing to assay region 271, accumulating at region 281.

Figure 11:
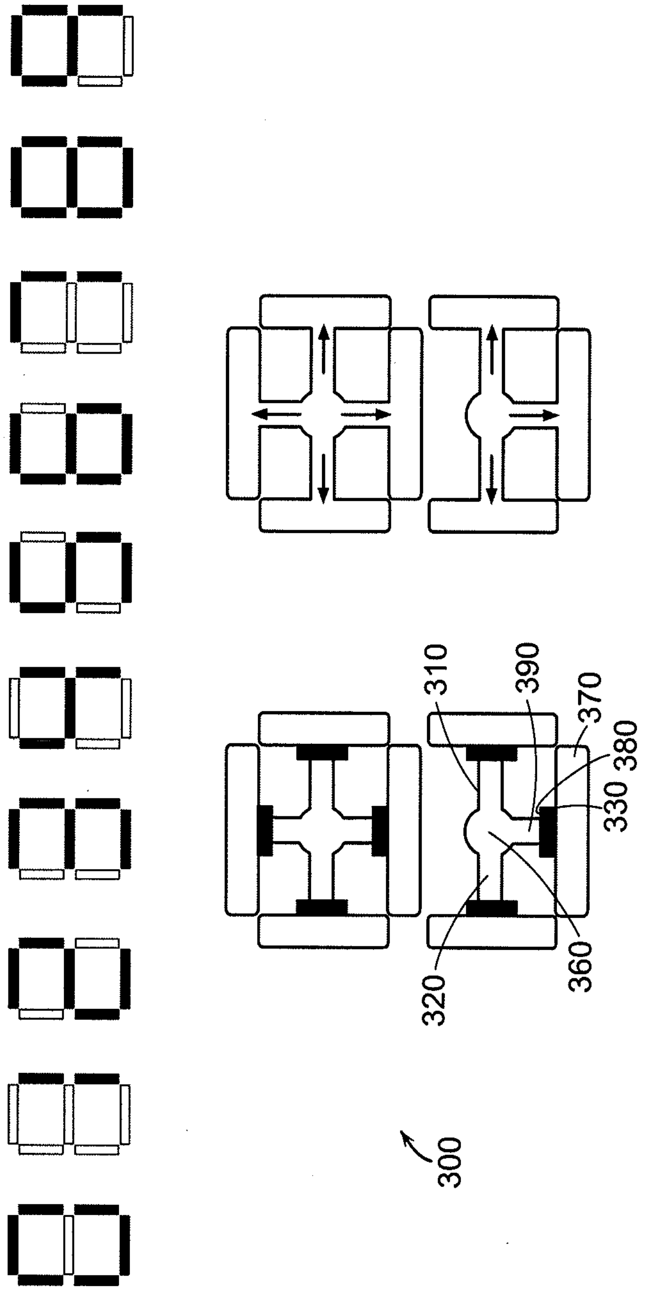
FIG. 11 is a schematic of a 3-D programmable microfluidic device.

FIG. 11 is a schematic illustration of a device 300 that includes a seven-segment liquid display, which can be used to display all numbers from 0 to 9. Device 300 includes patterned hydrophobic barrier 310, porous, hydrophilic substrate 320, and conductive material layers 330. The hydrophobic barrier 310 defines display regions 370, minor channel regions 390, and main channel region 360, which wicks fluid by capillary action to display regions 370 through minor channel regions 390. When electric current is applied to conductive material layer 330, the fluid sample wicks through main channel region 360 to region 380, where conductive material layer 330 contacts hydrophobic barrier 310, and does not flow into display regions 370. By turning current on and off to conductive material layers 330, fluid movement into display regions 370 can be controlled to display a particular number 0 to 9.

These devices present many advantages. For example, the devices use only a heating element (e.g., a flat, 30-μm-thin wire) to control the flow of the liquid in the channel. There are no mechanical valves or stoppers to control the flow of the fluid in the channel. The device has simple, thin and flat heating wires that "act" as a valve/switch. These valves/switches can direct the liquid very precisely and can "hold" (stop) the liquid in one position for hours (more than 2 h). With this method, the rate, direction and path of the flow can be controlled. This device is lightweight and thin, and can be bent or flexed. Paper is hydrophilic and chemically inert, can convey the liquid without external pumps due to the capillary forces. Paper channels are biocompatible. Paper can be chemically modified or functionalized to immobilize for example, capturing agents. Further, the fabrication process is inexpensive and can be done within an hour.

Microfluidic Devices for Measuring Electrolyte Concentrations in Fluid Samples

In one aspect, a microfluidic device for measuring salt concentrations in fluidic samples is described. The microfluidic device contains a patterned hydrophilic substrate with patterned hydrophilic regions, electrically conductive material pathways deposited onto the hydrophilic substrate, electronic components attached to the electrically conductive material pathways, and a microfluidic channel for depositing a fluid sample within one of the hydrophilic regions. The patterned hydrophilic substrate contains a fluid-impermeable barrier which substantially permeates the thickness of the hydrophilic substrate and defines boundaries of one or more hydrophilic regions within the hydrophilic substrate, as described herein.

A variety of electrical components can be attached to the electrically conductive material pathways. Non-limiting examples of electronic components include integrated circuits, resistors, capacitors, transistors, diodes, mechanical switches, batteries, and external power sources. Non-limiting examples of batteries include button cell (watch) battery. Non-limiting examples of external power source include an AC voltage source. The electrical components can be attached using, e.g., known adhesives. In certain embodiments, a commercially available two-part conductive adhesive (Circuit Specialists Inc.) is prepared by mixing equal volumes of the components in a Petri dish. This adhesive can be used immediately after mixing and is applied to the conductive material pathways using a syringe needle. Discrete electronic components are bonded to the metallic pathways by pressing the terminals of the electronic component on the adhesive.

The microfluidic channel for depositing a fluid sample can be any of the hydrophilic regions that is in contact with the conductive material pathways. The microfluidic channel for depositing a fluid sample, the conductive material pathways, and the electronic components are fabricated in such a way that when a fluid sample is introduced to the microfluidic channel, it came into contact with the conductive material pathways to complete a circuit containing the fluid, the conductive material pathways, and the electric components. In one or more embodiments, a fluid sample containing salt is introduced to the microfluidic channel. The concentration of salt within the fluid sample determines the resistance of the fluid sample, which in turn determines the electrical current of the circuit. In certain embodiments, a light-emitting diode (LED) is attached to the conductive material pathways. In certain specific embodiments, a fluid sample with high salt concentration and low resistance is introduced to the microfluidic channel and are in contact with the conductive material pathways. An electrical current passes through the circuit, a sufficient voltage is built across the LED, and the LED is turned on. In certain other specific embodiments, a fluid sample with low salt concentration and high resistance is introduced to the microfluidic channel and are in contact with the conductive material pathways. An insufficient voltage is built across the LED, and the LED remains on.

In other embodiments, a portion of the microfluidic channel for depositing a fluid sample is sealed from air to limit evaporation of the fluid sample during use after the assembly of the device. The portion sealed can be 50%, 60%, 70%, 80% 90%, or 95% of the microfluidic channels. In certain embodiments, the portion of the microfluidic channel is sealed by applying scotch tape to either side of the device. In certain other embodiments, the section of the microfluidic channel for depositing the fluid sample is not sealed. In certain specific embodiments, the section of the microfluidic channel adjacent to the edge of the patterned hydrophilic substrate is not sealed so that it could serve as the entrance to the microfluidic channel for depositing the fluid sample.

Figures 4A, 4B, 4C:
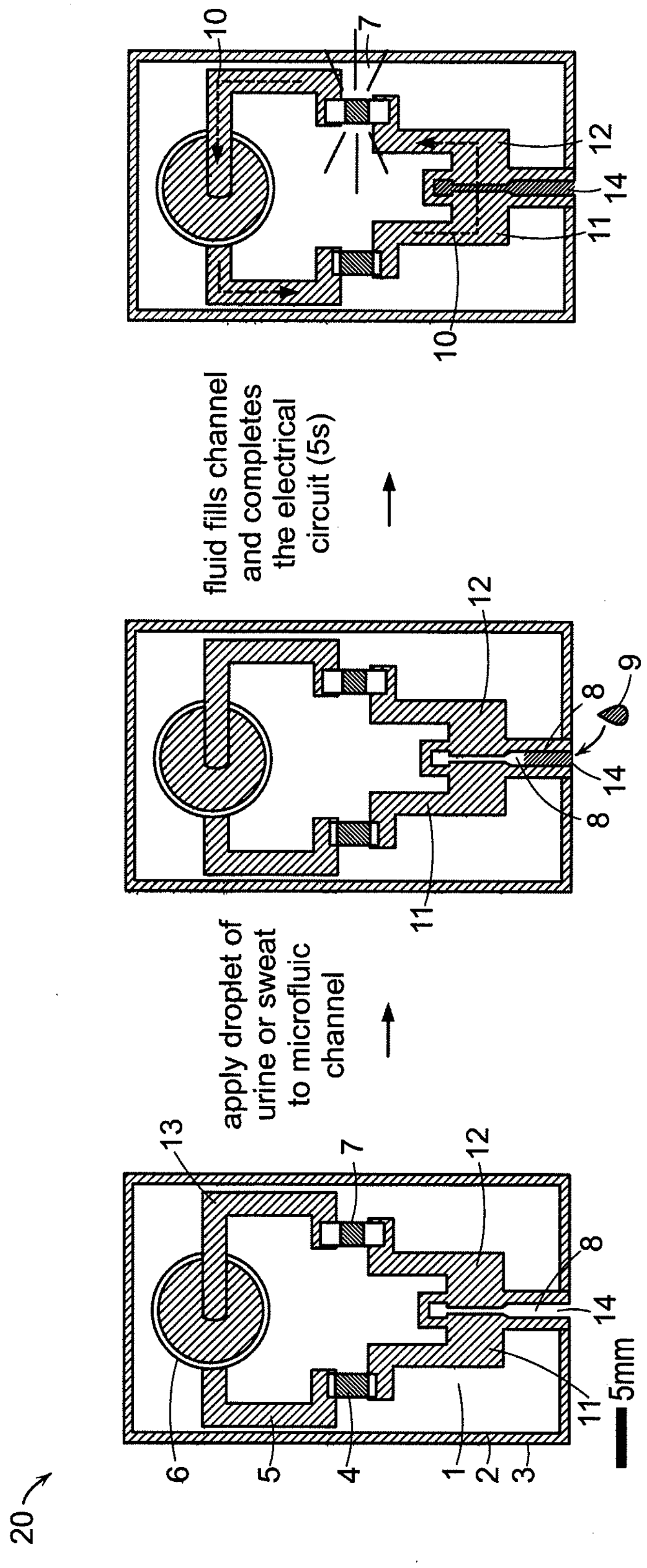
FIG. 4 is a schematic diagram of a paper-based microfluidic device and its use to measure dehydration.

In one specific embodiment, a microfluidic device 20 made out of patterned paper for measuring salt concentrations in fluidic samples is described with reference to FIG. 4. As shown in FIG. 4A, microfluidic device 20 contain patterned paper 1, metallic pathways 5, 11, 12, 13, electric components 4 and 7, and a microfluidic channel 8. Paper 1 is patterned by photoresist 2 using any of the methods described in WO2008/049083, the contents of which are hereby incorporated by reference. Metallic pathways 5, 11, 12, 13 are deposited onto paper substrate 1. A resistor 4 (100 kΩ) to modulate the current is attached to metallic pathways 5 and 11. A button cell (watch) battery 6 to supply the electrical current is attached to metallic pathways 5 and 13. A light-emitting diode (LED) 7 is attached to metallic pathways 12 and 13. A microfluidic channel 8 defined by part of photoresist 2 resides between metallic pathways 11 and 12 so that when a fluid sample is introduced into the microfluidic channel 8, a circuit is completed consisting the fluid sample, metallic pathway 11, resistor 4, metallic pathway 5, button cell battery 6, metallic pathway 13, LED 7, and metallic pathway 12. A plastic tape 3 is used to seal a portion of the microfluidic device as shown in FIG. 4A with edge 14 of the microfluidic channel 8 left unsealed. As shown in FIG. 4B, a fluid sample 9 is introduced to the edge 14 of the microfluidic channel 8. The fluid sample is wicked to fill the microfluidic channel 8 so that metallic pathways 11 and 12 are now electrically connected as shown in FIG. 4C. When the fluid sample 9 has low resistance, an electrical current 10 passes through the circuit, a sufficient voltage is built across LED 7, and LED 7 is turned on. In this embodiment, microfluidic channel 8 is 1 mm wide and the fluid sample 9 can be a urine or sweat sample with a volume of 50-100 μL supplied by a patient.

Patients suffering from dehydration have bodily fluids (e.g., sweat and urine) with higher concentration of NaCl than patients who are adequately hydrated. These concentrated salt solutions, in turn, have a lower electrical resistance than fluids with low salt concentration. Dehydration can be measured using the device described in this embodiment by passing an electrical current through the metallic pathways and the fluid sample 9 in the microfluidic channel 8. The device 20 measures the resistance of the fluid sample 9, and therefore, the level of dehydration in the patient. When fluid of high salt content (e.g., indicative of dehydration) fills the channel, the resistance of the circuit contributed by the fluid sample 9 is low, allowing sufficient voltage to build across (bias) LED 7, turning it on. This can indicate that a patient may be dehydrated. When fluid of low salt content (e.g., indicative of adequate hydration) fills the channel 8, the resistance of the circuit contributed by the fluid sample 9 is high, preventing sufficient voltage to build across the LED 7 and the LED 7 remains off, indicating that the patient is likely adequately hydrated. The resistor 4 is used to limit the current of the circuit, and to match the threshold voltage bias necessary to illuminate the LED 7 with the minimum concentration of salt in a biological sample, e.g., urine or sweat, e.g., indicative of dehydration.

The microfluidic device described functions without any external equipment and is lightweight and portable (the flat profile of the device makes it easy to stack and to store in binders, folders or other inexpensive and ubiquitous carrying cases already available for paper. The microfluidic device described are disposable and, therefore, more resistant to contamination than reused assays. The microfluidic device described are biodegradable and can be disposed of safely by incineration. The microfluidic device described requires only very small volumes of the sample fluid. In certain embodiments, only about 15 μL of urine, sweat, or other bodily fluids is required for analysis. In addition, the microfluidic device described can enable quick diagnoses. In certain embodiments, dehydration in patients can be diagnosed in less than 10 s from the time of applying a droplet of urine or sweat to the microfluidic device.

Porous, Hydrophilic Substrates

Any porous, hydrophilic substrate that wicks fluids by capillary action can be used as the substrate in the methods and devices described herein. Nonlimiting examples include cellulose and cellulose acetate, paper (e.g., filter paper and chromatography paper), cloth, and porous polymer film.

Preferably, the porous, hydrophobic substrate is paper. Paper can be patterned easily into regions of hydrophilic paper demarcated by walls of hydrophobic polymer; is hydrophilic and wicks fluids by capillary action, so no external pump is needed to move fluids within the microfluidic channels; is available with a variety of pore sizes that are useful for filtering solid contaminants and particulates from a fluid; is thin and lightweight; is very inexpensive and is available throughout the world; can be incinerated easily for disposal of hazardous waste after an assay; and can be modified covalently to alter the chemistry (and function) of an assay device.

Methods of Patterning

Exemplary methods for patterning hydrophobic barriers are described in WO2008/049083. For example, some embodiments of the assay devices are made using photolithography by saturating the porous, hydrophilic substrate with photoresist, exposing the saturated substrate to a predetermined pattern of light, and removing the photoresist based on the pattern, forming hydrophobic barriers made of photoresist. The pattern of the light can be selected to define assay regions, channel regions, sample deposition regions, and the like, the boundaries of which are at least partially defined by the hydrophobic barriers. Such methods provide a significantly high feature resolution. For example, these photolithographic techniques can be used to make barriers having a thickness between about 1 mm and about 100 μm, e.g., between about 300 μm and 100 μm, or even smaller. Additionally, the techniques can form features that do not vary significantly along their length, e.g., barriers having widths that vary by less than about 10%, by less than about 5%, or even less, along their length. Conversely, channels defined by such barriers will also have widths that do not vary significantly along their length, e.g., by less than about 10%, by less than about 5%, or even less, along their length.

Methods of Depositing Electrically Conductive Materials

In one aspect, microfluidic devices which incorporate electrically conductive materials onto hydrophilic substrates is described. Deposition of electrically conductive materials onto hydrophilic substrates of the microfluidic devices using a variety of methods is described.

Hydrophilic substrates can be any substrate that wicks fluids by capillary action. Non-limiting examples of hydrophilic substrates include nitrocellulose, cellulose acetate, paper, cloth, and porous polymer film. Non-limiting examples of paper include filter paper and chromatographic paper.

Non-limiting examples of electrically conductive materials include metal, conductive polymers, conductive grease, conductive adhesives, any other material that is electrically conductive, or a combination thereof. In one or more embodiments, the conductive materials include metal. Non-limiting examples of metals include Sn, Zn, Au, Ag, Ni, Pt, Pd, Al, In, Cu, or a combination thereof. In other embodiments, the conductive materials include conductive polymers. Non-limiting examples of conductive polymers include polyacetylenes, polypyrroles, polyanilines, poly(thiophene)s, poly(fluorene)s, poly(3-alkylthiophene)s, polytetrathiafulvalenes, polynaphthalenes, poly(p-phenylene sulfide), poly(para-phenylene vinylene)s, or any combination or derivative thereof. In yet other embodiments, the conductive materials include conductive grease, conductive adhesives or any other material that is electrically conductive.

A variety of deposition methods could be used to deposit electrically conductive materials onto the hydrophilic substrates of the microfluidic devices. Non-limiting examples of the deposition methods include depositing conductive materials using stencils, depositing conductive materials by drawing conductive pathways, depositing conductive materials by inkjet or laser printing, depositing conductive materials by attaching commercially available or homemade conductive material tapes onto the hydrophilic substrates, depositing conductive materials by drawing conductive pathways, or depositing conductive materials by introducing conductive fluids onto the hydrophilic substrates or the hydrophilic channels of the microfluidic devices. Alternatively, conductive materials could be embedded in the pulp or fibers for manufacturing the hydrophilic substrates to allow for manufacturing hydrophilic substrates containing conductive materials.

In one or more embodiments, the conductive materials are deposited onto the hydrophilic substrates of the microfluidic devices using stencils by a variety of techniques.

Stencils contain a pattern of holes or apertures through which conductive materials could be deposited onto the hydrophilic substrates. Alternatively, in a etching process, stencils contain a pattern of holes or apertures through which conductive materials could be etched to form a pattern of metal on the hydrophilic substrates. Stencils could be made from a variety of materials such as metal, plastic, or patterned layers of dry-film resist. Non-limiting examples of metals for manufacturing stencils include stainless steel and aluminum. Non-limiting examples of plastic for manufacturing stencils include mylar. Alternatively, patterned layers of dry-film resist can be used as stencils. In one or more embodiment, metals or plastics are used to manufacture stencils and patterns of metallic pathways can be designed on a computer using a layout editor, (e.g., Clewin, WieWeb Inc.) and stencils based on the design can be obtained from any supplier (e.g., Stencils Unlimited LLC (Lake Oswego, Oreg.)). In certain embodiments, the stencil can be removed from the paper after deposition. In certain other embodiments, one side of the stencil is sprayed with a layer of spray-adhesive (e.g., 3M Photomount, 3M Inc.) to temporarily affix the stencil to the paper substrate. After deposition, the stencil can be peeled away from the paper. The stencils can be reused multiple times, e.g., more than 10 times. In other embodiments, patterned layers of dry-film resist can be used as stencils. Dry film resist can be patterned when exposed to UV light through a transparency mask and developed in dilute sodium hydroxide solution. The patterned dry-film resist can be attached to a coating sheet of plastic or directly affixed to the hydrophilic substrates by pressing the resist-side to the surface of the hydrophilic substrates and passing multi-sheet structure through heated rollers in a portable laminator (Micro-Mark, Inc). The coating sheet of plastic can then be peeled away, resulting in a sheet of paper with dry film resist patterned on one side.

A variety of techniques could be used to deposit electrically conductive materials onto the hydrophilic substrates of the microfluidic devices through stencils. Non-limiting examples of such techniques include evaporating through stencils, sputter-depositing through stencils, spray-depositing through stencils, squeegeeing through stencils, or evaporating or sputter-depositing a thin layer of conductive material through stencils followed by developing a thicker layer of conductive material by electrodeposition or electroless deposition. Alternatively, a conductive material is first deposited onto a hydrophilic substrate by evaporation, sputter-deposition, spray-deposition, or squeegee. A stencil is then applied and the part of the conductive material that is not protected by the stencil is etched to form a pattern of conductive material on the hydrophilic substrates.

In one or more embodiments, conductive materials are evaporated onto the hydrophilic substrates of the microfluidic devices through stencils. Evaporation is a method of thin film deposition in which the source material is evaporated in a vacuum. The vacuum allows vapor particles to travel directly to the target object (substrate), where they condense back into a solid state. Detailed descriptions of evaporation deposition can be found in S. A. Campbell, *Science and Engineering of Microelectronic Fabrication*, Oxford University Press, New York (1996), which is hereby incorporated by reference in its entirety. Evaporating requires a high vacuum, is applicable to a variety of metals, and can deposit metal at rates of up to 50 nm/s. In certain embodiments, conductive materials such as metals are evaporated onto the hydrophilic substrates through stencils made of metal, plastic, or photoresist. In certain other embodiments, conductive materials are evaporated onto the hydrophilic substrates through stencils made of metal or plastic based on a silk-screen soaked in photoresist. In yet certain other embodiments, a thin layer of conductive materials is evaporated onto the hydrophilic substrates and then the a thicker layer of conductive materials is deposited by electrodeposition or electroless deposition. In certain specific embodiments, metal is evaporated on paper using an e-beam evaporator. Non-limiting examples of metal in these embodiments include 100% Sn, 100% In, 100% Au, 100% Ag, 52% In-48% Sn Eutectic, 100% Ni and 100% Zn.

In other embodiments, conductive materials are sputter-deposited onto the hydrophilic substrates of the microfluidic devices through stencils. Sputter deposition is a physical vapor deposition method of depositing thin films by sputtering, i.e., ejecting, material from a source onto a substrate, e.g., a hydrophilic substrate. Detailed descriptions of sputtering deposition can be found in S. A. Campbell, *Science and Engineering of Microelectronic Fabrication*, Oxford University Press, New York (1996). Sputter-deposition is usually performed at a lower vacuum (>75,000 μTorr) and deposits conductive materials such as metals at a lower rate than evaporation (e.g., 1 nm/s for Au, with lower rates and higher energy requirements for other metals). In certain embodiments, conductive materials such as metals are sputter-deposited onto the hydrophilic substrates through stencils made of metal, plastic, or photoresist. In certain other embodiments, conductive materials are sputter-deposited onto the hydrophilic substrates through stencils made of metal or plastic based on a silk-screen soaked in photoresist. In yet certain other embodiments, a thin layer of conductive materials is sputter-deposited onto the hydrophilic substrates and then the a thicker layer of conductive materials is deposited by electrodeposition or electroless deposition. In certain specific embodiments, metal is deposited onto paper by sputtering using a Cressington 208HR benchtop sputter coater. Non-limiting examples of metal in these embodiments include 100% Pt, 100% Au, 80% Pd/20% Pt, 100% Ag, 100% Ni, 100% Al and 100% Sn. In another specific embodiment, Au (gold) is sputtered onto a hydrophilic substrate. Gold has an electrical conductivity similar to that of copper or aluminum (electrical conductivity=$45.17\times10^{6}$ 1/Ωm, at 20° C.). Gold wires with a small cross sectional area (50 nm×1 mm) over several centimeters long can form conductive metallic pathways with high resistance (>100Ω). Such gold wires can be heated to high temperatures (about 90° C.) using modest voltages (about 5 V) and currents (about 55 mA), which can be supplied easily by portable alkaline or Li-ion batteries. Alternatively, a section of tape can be affixed directly onto the hydrophilic substrates and then gold is sputter-deposited through a mask onto the tape.

In yet other embodiments, conductive materials are spray-deposited onto the hydrophilic substrates of the microfluidic devices through stencils. Spray-deposition is quick and inexpensive and can be applied at room temperature without specialized equipment. Also, because of its large coating thickness, spray deposition of metal can be used to build electrically conductive pathways on very rough surfaces including toilet paper, paper towel, or even woven fabric. The spray is applied via an airbrush or an aerosol container consisting of flakes of conductive materials such as metals suspended in an acrylic base. In certain embodiments, conductive materials such as metals are spray-deposited onto the hydrophilic substrates through stencils made of metal, plastic, or photoresist. In certain other embodiments, conductive materials are spray-deposited onto the hydrophilic substrates through stencils made of metal or plastic based on a silk-screen soaked in photoresist. In certain specific embodiments, Ni or Ag is sprayed onto a substrate and curing at room temp (10 min) produces an electrically conductive surface (thickness=20-100 μm depending on number of passes, surface resistance=0.7 Ω/square for Ni, 0.01 Ω/square for Ag).

In yet other embodiments, conductive materials are squeegeed onto the hydrophilic substrates of the microfluidic devices through stencils. Non-limiting examples of electrically conductive materials that can by squeegeed onto the hydrophilic substrates include solder paste, conductive grease, conductive adhesive or conductive ink (metal or conductive polymer based). Squeegee techniques can be used to deposit conductive materials on the surface or into the inside of the hydrophilic substrates. In certain embodiments, conductive materials such as metals are squeegeed onto the hydrophilic substrates through stencils made of metal, plastic, or photoresist. In certain other embodiments, conductive materials are squeegeed onto the hydrophilic substrates through stencils made of metal or plastic based on a silk-screen soaked in photoresist.

In yet other embodiments, conductive materials are deposited onto the hydrophilic substrates of the microfluidic devices using a etching process through stencils. In certain embodiments the conductive material is first deposited onto the hydrophilic material by evaporation, sputter-deposition, spray-deposition, or squeegee. A stencil is then applied and the part of the conductive material deposited onto the hydrophilic substrates that is not protected by the stencil is etched, resulting in a pattern of the electrically conductive material on the hydrophilic substrate. In certain specific embodiments, conductive materials such as metals are deposited onto the hydrophilic substrates and then through stencils, the deposited metals are subjected to a reactive-ion etching process to remove the part of the metal deposit which is not protected by the stencil, resulting a pattern of metal on the hydrophilic substrates.

In yet other embodiments, conductive materials are deposited by drawing conductive pathways on hydrophilic substrates. In certain embodiments, metals are deposited onto the hydrophilic substrates using pens filled with conductive metal inks Non-limiting examples of metal in these embodiments include Ag and Ni. In certain other embodiments, conductive polymers are deposited onto the hydrophilic substrates using pens filled with conductive polymers. Drawing conductive pathways could deposit conductive materials both on the surface and inside the matrix of the hydrophilic substrates.

In yet other embodiments, conductive materials are deposited by inkjet or laser printing. In certain embodiments, conductive polymers are printed or plotted by inkjet or laser printing. In certain other embodiments, a conductive ink is printed or plotted by inkjet or laser printing.

In yet other embodiments, conductive materials are deposited by attaching commercially available or homemade conductive material tapes onto the hydrophilic substrates. In certain embodiments, commercially-available conductive tape is affixed onto the surface of the hydrophilic substrates. Non-limiting examples of commercially-available conductive tapes include copper tape. In certain other embodiments, homemade conductive tape is affixed onto the surface of the hydrophilic substrates. Non-limiting examples of homemade conductive tapes include plastic tape such as scotch tape coated with conductive materials by evaporation, sputter-deposition, spray-deposition or squeegee.

In yet other embodiments, conductive materials are deposited by introducing conductive fluids onto the hydrophilic substrates or the hydrophilic channels of the microfluidic devices. In certain embodiments, conductive fluids are wicked into the hydrophilic substrates or the hydrophilic channels. Non-limiting examples of conductive liquids include ionic solutions, metals, carbon-nanotube solutions, or conductive polymers.

In yet other embodiments, conductive materials could be embedded in the pulp or fibers for manufacturing the hydrophilic substrates to allow for manufacturing hydrophilic substrates with conductive materials deposited within. In certain embodiments, metals or other conductive materials are embedded in the pulp or fibers used for manufacturing paper.

In another aspect, electrical components are attached onto the hydrophilic substrates after the deposition of conductive materials. The electrical components can be attached using, e.g., known adhesives. In certain embodiments, a commercially available two-part conductive adhesive (Circuit Specialists Inc.) can be prepared by mixing equal volumes of the components in a Petri dish. This adhesive can be used immediately after mixing and is applied to the conductive material pathway using a syringe needle. Discrete electronic components are bonded to the metallic pathways by pressing the terminals of the electronic component on the adhesive. Non-limiting examples of electronic components include integrated circuits, resistors, capacitors, transistors, diodes, mechanical switches, and batteries.

Figure 2:
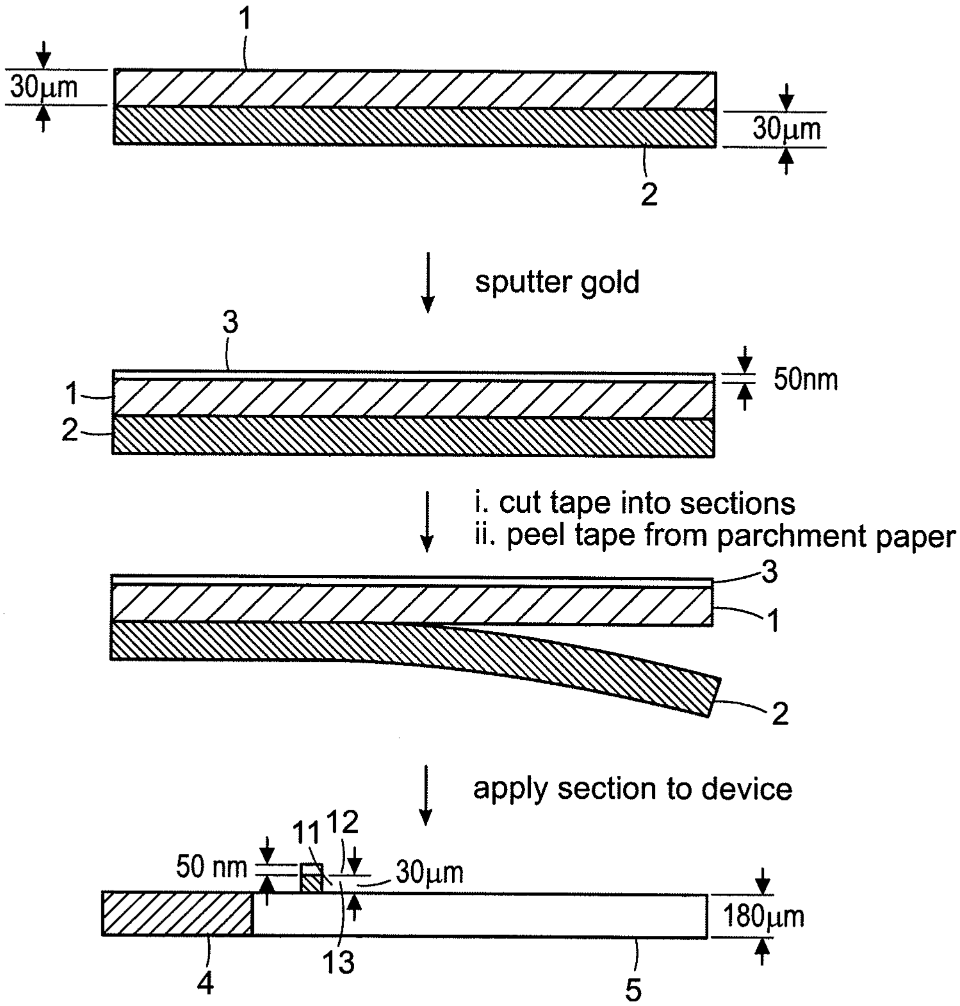
FIG. 2 is a schematic illustrating a method for fabricating prototype μ-PAD devices for concentrating analytes in fluids.

FIG. 2 schematically illustrates a method for depositing conductive materials to make an assay device described herein. As shown in FIG. 2, an insulating layer 1 (30 μm thick) is first attached to a porous, hydrophilic substrate 2 (30 μm thick). A conductive metal layer 3 (50 nm thick) is then deposited onto the insulating layer 1 by sputter deposition. The formed sandwich of conductive metal-insulating layer-porous, hydrophobic substrate layers is then cut into sections and within one of the sections, the insulating layer 1 (with the conductive metal layer 3 attached) is detached from porous, hydrophilic substrate 2 to form a conductive metal-insulating layer assembly 11 containing 12, a section of the conductive metal layer, and 13, a section of the insulating layer. The conductive metal-insulating layer assembly 11 is then attached to a patterned porous, hydrophilic substrate 5 with hydrophobic material 4 permeating the thickness of selected portions of the patterned porous, hydrophilic substrate 5. The formed sandwich of conductive metal-insulating layer-porous, hydrophilic substrate layers can be cut into sections with a variety of shapes and sizes and the insulating layers within the sections (with the conductive metal layer attached) can be detached from the porous, hydrophilic substrate to form conductive metal-insulating layer assemblies with different shapes and sizes.

Detection Reagents

The bounded regions of the hydrophilic substrate can be used to define one or more assay regions in an assay device. The assay regions of the bioassay device can be treated with reagents that respond to the presence of analytes in a biological fluid and that can serve as an indicator of the presence of an analyte. In some embodiments, the response to the analyte is visible to the naked eye. For example, the hydrophilic substrate can be treated in the assay region to provide a color indicator of the presence of the analyte. Indicators may include molecules that become colored in the presence of the analyte, change color in the presence of the analyte, or emit fluorescence, phosphorescence, or luminescence in the presence of the analyte. In other embodiments, radiological, magnetic, optical, and/or electrical measurements can be used to determine the presence of proteins, antibodies, or other analytes.

In some embodiments, to detect a specific protein, an assay region of the hydrophilic substrate can be derivatized with reagents, such as small molecules, that selectively bind to or interact with the protein. Or, for example, to detect a specific antibody, an assay region of the hydrophilic substrate can be derivatized with reagents such as antigens, that selectively bind to or interact with that antibody. For example, reagents such as small molecules and/or proteins can be covalently linked to the hydrophilic substrate using similar chemistry to that used to immobilize molecules on beads or glass slides, or using chemistry used for linking molecules to carbohydrates. In alternative embodiments, the reagents may be applied and/or immobilized by applying them from solution, and allowing the solvent to evaporate. The reagents can be immobilized by physical absorption onto the porous substrate by other non-covalent interactions. In general, a wide variety of reagents can be used with the assay devices to detect analytes, and can be applied by a variety of suitable methods. These reagents could include antibodies, nucleic acids, aptamers, molecularly-imprinted polymers, chemical receptors, proteins, peptides, inorganic compounds, and organic small molecules. These reagents could be adsorbed to paper (non-covalently through non-specific interactions), or covalently (as either esters, amides, imines, ethers, or through carbon-carbon, carbon-nitrogen, carbon-oxygen, or oxygen-nitrogen bonds).

However, the interaction of some analytes with some reagents may not result in a visible color change, unless the analyte was previously labeled. The device can be additionally treated to add a stain or a labeled protein, antibody, nucleic acid, or other reagent that binds to the target analyte after it binds to the reagent in the assay region, and produces a visible color change. This can be done, for example, by providing the device with a separate area that already contains the stain, or labeled reagent, and includes a mechanism by which the stain or labeled reagent can be easily introduced to the target analyte after it binds to the reagent in the assay region. Or, for example, the device can be provided with a separate channel that can be used to flow the stain or labeled reagent from a different region of the paper into the target analyte after it binds to the reagent in the assay region. In one embodiment, this flow is initiated with a drop of water, or some other fluid. In another embodiment, the reagent and labeled reagent are applied at the same location in the device, e.g., in the assay region.

Biological Samples

The microfluidic systems described herein can be used for assaying sample fluids. Biological samples that can be assayed using the diagnostic systems described herein include, e.g., urine, whole blood, blood plasma, blood serum, cerebrospinal fluid, ascites, tears, sweat, saliva, excrement, gingival cervicular fluid, or tissue extract.

In some embodiments, a single drop of liquid, e.g., a drop of blood from a pinpricked finger, is sufficient to perform assays providing a simple yes/no answer to the presence of an analyte, or a semi-quantitative measurement of the amount of analyte that is present in the sample, e.g., by performing a visual or digital comparison of the intensity of the assay to a calibrated color chart. However, in order to obtain a quantitative measurement of an analyte in the liquid, a defined volume of fluid is typically deposited in the device. Thus, in some embodiments, a defined volume of fluid (or a volume that is sufficiently close to the defined volume to provide a reasonably accurate readout) can be obtained by patterning the paper to include a sample well that accepts a defined volume of fluid. For example, in the case of a whole blood sample, the subject's finger could be pinpricked, and then pressed against the sample well until the well was full, thus providing a satisfactory approximation of the defined volume.

Applications

The microfluidic systems to measure salt concentrations in solutions described herein can be used in a number of different applications. For example, they can be useful for pediatric physicians (for diagnosis of dehydration in infants or other patients in which it is difficult to obtain large volumes of urine); physicians working in resource-poor settings such as developing countries (for diagnosing dehydration in environments where the cost of the assays or the availability of electricity for running instruments are of primary concern); physicians working in emergency or point-of-care environments (as a method for detecting dehydration rapidly); nurses or caregivers in nursing homes (for testing dehydration in the elderly); military technologists (for monitoring dehydration in soldiers); athletes, trainers, or sports physicians/technicians (for testing dehydration in athletes "on-the-field" in practice or in competition); veterinarians (for testing dehydration in domestic pets, livestock, racehorses, or other animals.); farmers or agricultural scientists/engineers (for testing dehydration in plants and animals); environmental scientists (for testing the concentration of salt in water); and chemists, bioengineers, or chemical engineers (as a blueprint for building other disposable electronic-microfluidic hybrid devices in paper substrates).

The microfluidic systems incorporating switches and valves described herein can be used in many applications. For example, they can be adapted to perform reactions in channels (e.g., PCR, nucleic acid synthesis). Further, paper devices with heating elements can be used by chemists for conducting (bio)chemical reaction within such system (e.g., as a lab-on-a-chip device). In some embodiments, the product can be directly synthesized in the reacting chamber, purified by chromatography (simply by migration to other channels), and separated from the chip by cutting a piece of paper.

In other embodiments, the devices incorporating switches and valves can be used as a model system in understanding the flow of the liquid, heat transfer and its influence on the stream in porous media (see FIGS. 10 and 11). The devices can also be a used to investigate the presence of small molecules in versatile fluids (e.g., blood, urines, saliva, and water) by concentrating them directly before adding a fresh reagent. The switches can enable one to perform the reaction next to a control analyte or to compare how the concentration influences the detection (e.g., while one switch is on and the analyte in the fluid is concentrating, the other channel is filled with non-concentrated analyte, and at the end analytes in both channels can be reacted with the reagent). These devices can also be used in microfluidic experiments when the number of different liquids or reagents that can be added to the system, either in doses or simultaneously, is limited.

The use of metals in paper as microfluidic devices can also be adapted and used in any of the following applications: pumping fluids in paper; concentrating analytes in paper by evaporation; "switching" fluids in paper or controlling the directional flow of fluids, or turning on/off the flow of fluids in paper; performing electrochemical reactions in paper (e.g., redox); paper-based batteries or fuel cells; sensing temperature of fluids in paper; heating fluids in paper (e.g., for reactions or incubation of cells); PCR in paper; cooling fluids in paper (e.g., when metal is used as a conductor of "cold" from a cooling device such as a Peltier cooler); concentrating magnetic fields in paper microfluidic devices (e.g., nickel pattern+external permanent magnet); applying magnetic fields in paper for separations, trapping, or capturing particles or analytes; applying electrical or magnetic fields in paper for mixing (e.g., using small particles that shake around); electrophoresis in paper microfluidic channels; capacitive detection in paper (e.g., sense difference in dielectric); sensing the ionic resistance in paper (e.g., for detecting salt content); sensing the electrical resistance in paper (e.g., a paper diagnostic device where silver reduction in a microfluidic channel produces a conductive pathway of given resistance proportional to the analyte being detected); complex electrically-actuated fuses (e.g., where the microfluidic channels contain an explosive, e.g., gasoline); self-destructive paper diagnostics (e.g., where the fuse is actuated by the electronics eliminating the need for an external spark or flame); and portable, remote-sensing diagnostic devices (e.g., diagnostics that take measurements and then send signals long distances via RF communication).

The invention is further illustrated by the following examples. The examples are provided for illustrative purposes only. They are not to be construed as limiting the scope or content of the invention in any way.

EXAMPLES

Example 1

Preparation and Use of Paper Microfluidic Device for Analyte Concentration

Fabricating a Paper Microfluidic Device

The prototype μ-PADs was fabricated in a two step process (see FIG. 2). The μ-PADs were prepared in a two-step process that involved creating patterns of hydrophobic polymer in paper, and patterning conductive gold pathways onto the paper-based microfluidic devices.

First, the microfluidic channels were formed in Whatman filter paper 1 using photolithography and SU-8 photoresist, as described previously (Martinez et al., Angew. Chem. Int. Ed., Eng. 46:1318-1320, 2007). Briefly, this process involved embedding SU-8 photoresist into Whatman filter paper 1, drying the paper to remove the cyclopentanone in the SU-8 formula, and then irradiating the paper for around 3.5 min (using a 100 W mercury lamp) through a pattern of black ink printed onto a transparency. The paper was heated at 90° C. for 10 min, soaked in propylene glycol methyl ether acetate (3×5 min) and methanol (3×5 min), and dried.

The gold conductive pathways were then patterned onto the paper-based microfluidic device by first preparing the wires, and then affixing them to the microfluidic device. For these devices, gold was patterned onto tape and the tape was cut into appropriately sized conductive pathways for affixing to the devices. Specifically, the wires were fabricated by affixing the sticky side of Scotch® Transparent Tape to unbleached parchment paper, and by sputtering a 50 nm layer of gold onto the shinny side of the tape using a Cressington Model 208HR sputter coater set to 60 mA and 50 s sputtering time (see FIG. 2). The gold/tape/parchment paper composite was cut into sections sized appropriately for the μ-PAD (i.e., a straight section with dimensions of 30 μm×1 mm×22 mm for the single channel μ-PAD, and a continuous U-shaped section with dimensions of 30 μm×1 mm×21 mm at the base of the U, and 30 μm×1 mm×15 mm on the sides of the U for the multiple channel μ-PAD). The parchment paper was peeled from the gold/tape composite, and the tape was affixed to the paper-based microfluidic devices around 0.5 mm below the bottom of the detection zones. This distance was far enough from the detection zones to minimize transfer of heat from the wire to the reagents deposited in the zones.

Concentrating Aqueous Red Dye

The effectiveness of the device for concentrating an analyte was tested by concentrating an aqueous solution of 165 μM allura red AC (a red food coloring) using a single channel μ-PAD fabricated as described above. Alligator clips (micro flat alligator clips, Mueller Electric Inc.) were used to connect the gold wires on each device to a tunable current source (see FIG. 3*a*). In FIG. 3*a*, the allura red AC solution has reached the wire and has become slightly concentrated. Each metal wire had a resistance of around 100Ω. Passing current through the device (around 55 mA) for 5 s heated the metal. The temperature of the wire was measured using an IR Thermometer (FIG. 3*b*). The temperature of the paper on the back side of the μ-PAD (i.e., on the opposite side of the wire) was also measured, and an immediate increase of temperature of the channel from 23° C. to around 75±5° C. was observed when voltage was applied. There was an approximately 5° C. variation in the final temperature of the channel that reflected small differences in width of the gold wires.

Initially, the device was suspended above a 5 mL aqueous solution of allura red AC (165 μM). The aqueous solution then was raised until it contacted the bottom of the paper (with the current turned on). The aqueous solution wicked into the central channel of the device and reached the wire in 30-60 s. As the solution wet the hydrophilic channel adjacent to the wire, the temperature of the channel decreased by around 3-5° C. (at 23% relative humidity). The fluid did not continue wicking up the central channel beyond the wire when the channel was warmed above 60° C. Instead, the heat from the wire was absorbed by the solution, leading to evaporation of the water in proximity to the wire.

When the fluid evaporated, the allura red AC was concentrated in the portion of the channel aligned with the wire (FIG. 3*c*). The fluid continued to evaporate and the analyte became increasingly concentrated as long as current was passed through the μ-PAD. The channel underneath the wire was heated to ~70° C. Current (55 mA) was applied continuously for 13 min and then reduced to zero. After turning off the current, the channel cooled within seconds and the fluid wicked into the remaining portions of the device. In the orientation depicted in FIG. 3*c*, the gold wire was on the back of the devices. The location of the wire is highlighted by dotted lines in the photograph of the device after 1 min of heating. The concentrated allura red AC appeared as the dark material below the detection zone. In this example, the device was heated for a maximum of 13 min, but the device can be heated and the analyte concentrated until the fluid is consumed.

When the current was turned off, the channel cooled from 65-75° C. to 23° C. in less than 5 s. As soon as the channel cooled to ~40° C., the fluid began wicking into the remaining portions of the device. The close proximity of the wire to the detection zones ensured that the concentrated analyte moved as a plug with the liquid and remained concentrated as it filled the diamond-shaped regions (FIG. 3*c*).

Relationship Between Length of Heating and Concentration of Analyte

The relationship between the length of time that a sample was heated and the relative amount that the analyte was concentrated was measured by wicking 165 μM allura red AC in water into multiple μ-PADs. The devices were heated for different periods of time and then cooled to allow the fluid to fill the detection zones. The relative percent increase in color that collected in the ends of the devices was measured by photographing the dry devices and by obtaining the mean intensity of color for the terminal triangular region of each device using Adobe® Photoshop®. The triangular regions were scanned using the blue channel in Adobe® Photoshop®, and the relative percent increase in allura red AC was calculated using the following equation:

$$\text{relative \% increase} = \frac{\text{color}_{no\ heating} - \text{color}_{heating\ (n\ min)}}{\text{color}_{no\ heating}} \times 100$$

Figure 3D:
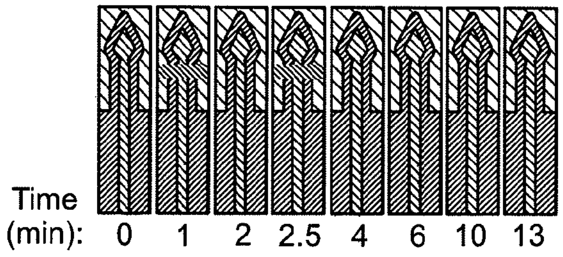
FIG. 3D is a series of representations of photographs of identical μ-PAD devices.
Figure 3E:
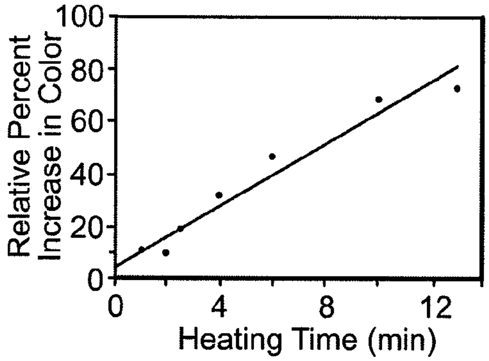
FIG. 3E is a graph of the relative percent increase in color in the triangular tips of heated devices over time.

The extent to which color developed in the triangular tips of the devices depended on the length of time that current was passed through the gold wire (FIG. 3*d*). In FIG. 3*d*, identical μ-PAD devices were heated for varying lengths of time and then cooled to allow the concentrated samples to wick into the pentagon-shaped ends of the devices. The heating time started when the fluid reached the wire in the central channel and ended when the current was reduced to zero. When the device was heated for short periods of time (1 min), the color was only 10% higher than devices run in the absence of applied current (FIG. 3*e*; the data were fit with a linear least-squares line described by the following equation: y=5.92×+3.81; $R^2$=0.96). When heated for 13 min, however, the color was 73% more intense than devices that were not heated.

Example 2

Figure 5:
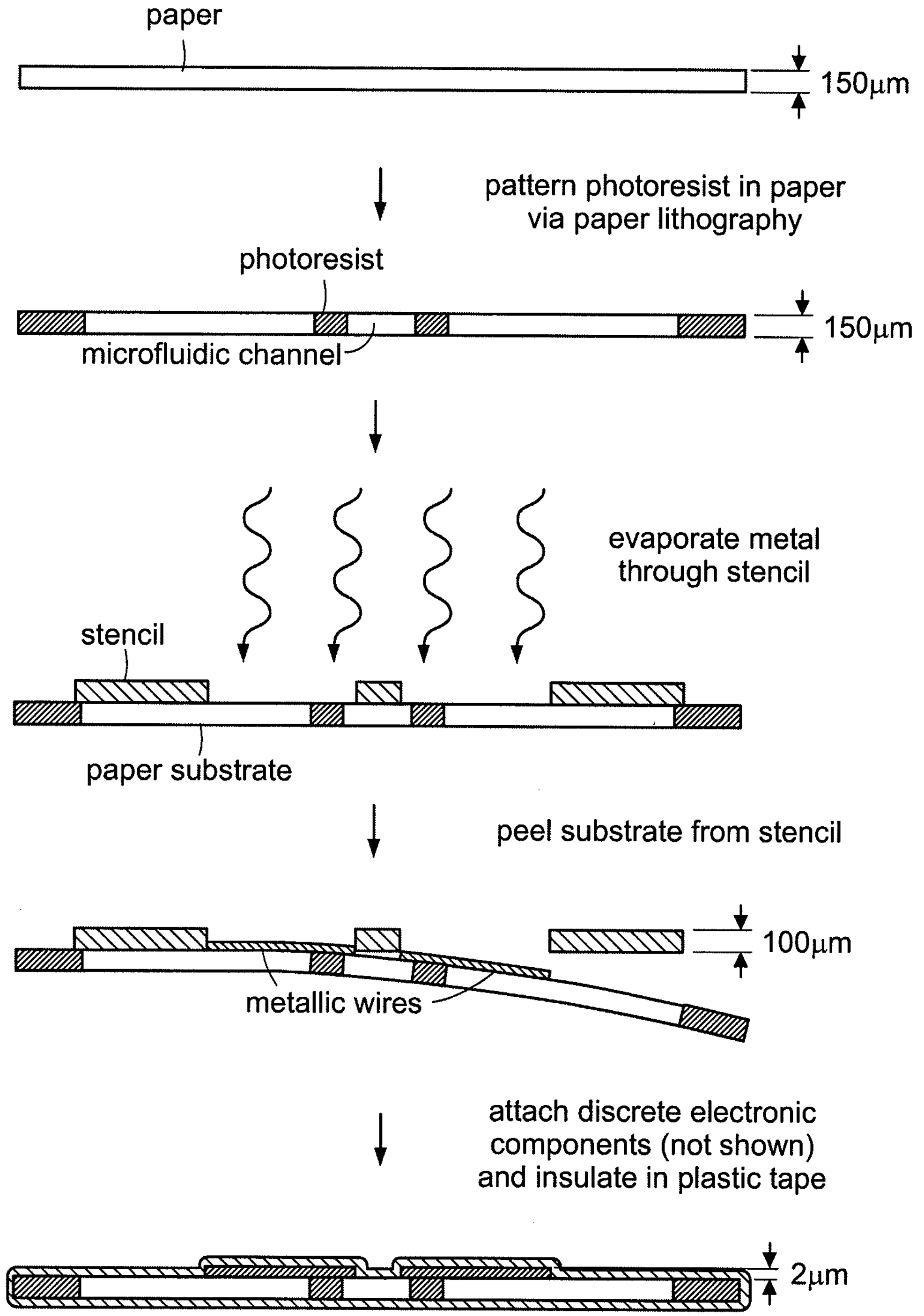
FIG. 5 is a schematic diagram of a method of fabricating a paper-based microfluidic device to measure dehydration.

Preparation and Use of Paper Microfluidic Device for Detecting Salt Concentration Fabricating a Paper Microfluidic Device Microfluidic channels were fabricated in filter paper (Whatman, Inc.) using a process described previously (Martinez et al., Angew. Chem. Int. Ed., Eng. 6:1318-1320, 2007) (see FIG. 5). The patterns for the microfluidic channels were designed on a computer using a layout editor (Clewin, WieWin Inc.) and a photomask was printed from the design using an inkjet printer and a transparency film. The microfluidic channels were patterned in Whatman filter paper 1 using the following process: (i) paper (2.5 cm×2.5 cm×200 μm) was soaked in resist (SU-8 2010, Microchem Inc.), and a rolling pin was used to press excess resist from the paper; (ii) the paper was dried for 10 min at 95° C., the photomask was clamped to the paper by pressing them together as a sandwich between two glass slides that were held together with binder clips, and the paper was exposed to UV light (100 W mercury spot lamp) through the photomask to transfer the pattern of the mask to the paper; and (iii) the paper was developed by soaking it in propylene glycol monomethyl ether acetate (2×10 min) and propan-2-ol (2×10 min).

Fabricating Metallic Wires on the Microfluidic Devices

Patterns of metallic pathways were designed on a computer using a layout editor (Clewin, WieWeb Inc.) and a stainless steel stencil was obtained from Stencils Unlimited LLC (Lake Oswego, Oreg.) based upon the design.

The metal was deposited on the paper-based microfluidic device by manually aligning the stencil to the features patterned in the paper, and by evaporating conductive metal (100% In) through the stencil. The metal was patterned on either side of the microfluidic channel and extended over the edges of the hydrophobic barrier defining the channel and into the hydrophilic channel, such that when fluid filled the microfluidic channel, it came into contact with the metal to complete the circuit.

After depositing the metal, 90% of the microfluidic channel was sealed from air by applying scotch tape to either side of the device. This step limits evaporation of fluid during use. The section of microfluidic channel adjacent to the edge of the paper was not sealed so that it could serve as the entrance to the microfluidic channel for the fluid.

Mounting Electronic Components to the Paper

The electronic components were attached to the device using a process described above. A commercially available two-part conductive adhesive (Circuit Specialists Inc.) was prepared by mixing equal volumes of the parts in a Petri dish. Immediately after mixing: (i) the adhesive was applied to the metallic pathways using a syringe and needle, and (ii) the electronic components—the resistor, LED, and battery—were bonded to the metallic pathways by pressing the terminals of the electronic components on the adhesive. The epoxy set in less than 15 min, forming permanent electrical connections between the components and the conductive pathways on the paper. The complete device comprised a 3 V button (watch) battery (Energizer Inc., $0.20), a resistor (Digikey Inc., $0.01) and a light-emitting diode (Lumex Inc. $0.08) (see FIG. 4).

Measuring the Electrical Resistance of Aqueous Salt Solution in a Paper-Based Microfluidic Channel Six identical microfluidic devices were fabricated as discussed above. The microfluidic channel in each device was filled with aqueous solutions containing different concentration of NaCl: 0 mM, 50 mM, 100 mM, 250 mM, 500 mM, and 1000 mM.

The electrical resistance of the fluid-filled microfluidic channel in each device was determined by connecting the metal wires fabricated on either side of the channel to a voltage source (BK Precision, Inc.) biased at 1 V, and by measuring the electrical current passing through the channel with a digital multimeter (Fluke, Inc.). The electrical resistance of the channel was obtained by dividing the bias voltage by the current.

Figure 6A:
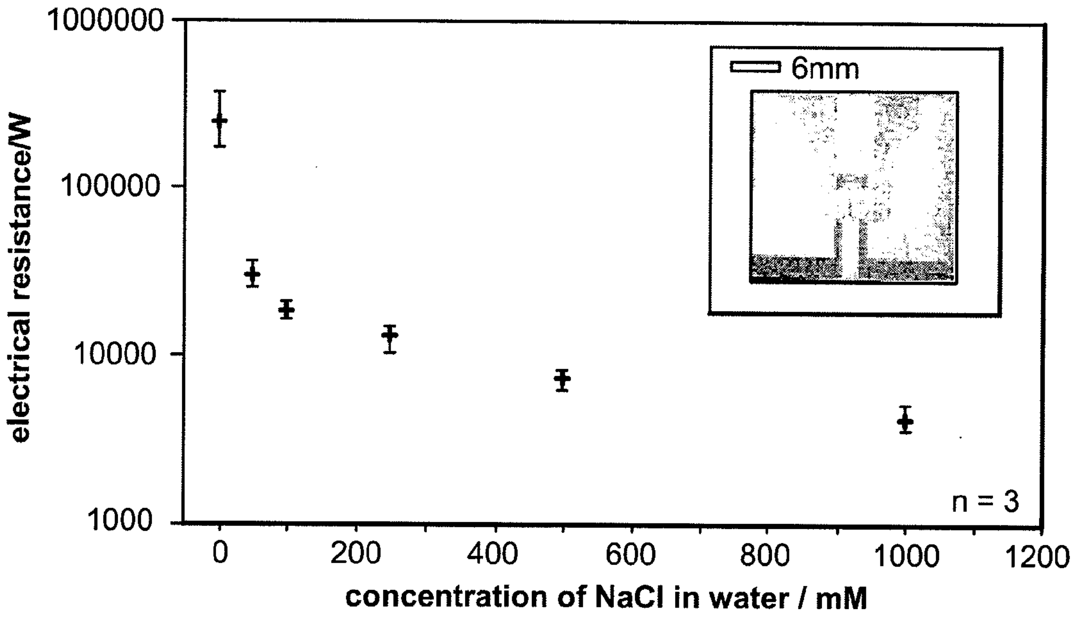
FIG. 6A is a graph of the electrical resistance of a microfluidic channel vs. the concentration of NaCl in the solution that fills the channel. Inset shows a representation of a photograph of the device used for the experiments.

FIG. 6*a* shows the steady-state resistance of the channel as a function of the concentration of NaCl in the solution. All values were collected at 60 s, at which the resistance that was measured was near steady state in all samples. The plot shows that the channel exhibited highest resistance when the water in the channel contained no added salt. As the concentration of salt in the solution was increased, the resistance of the channel decreased. Error bars represent the range of data across three experiments using three separate, identical devices.

Figure 6B:
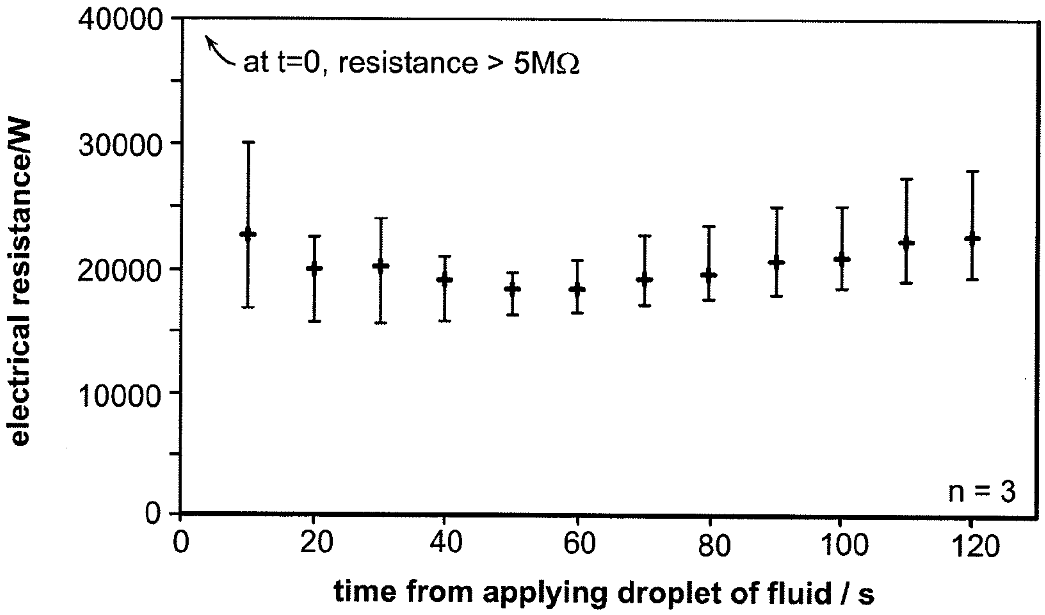
FIG. 6B is a graph of the electrical resistance of a microfluidic channel vs. time for a 100 mM solution of NaCl in water.

FIG. 6*b* shows the resistance of the channel as a function of time after applying the droplet of solution to the device. At t=0, the resistance of the channel was approximately 5 MΩ. Within 10 s, the resistance reduced to an approximate steady-state value of 20 kΩ. Error bars represent the range of data across three experiments using three separate, identical devices.

Example 3

Preparation and Use of Paper Microfluidic Device with Switches and Valves

Fabrication of the Devices

The microfluidic devices were fabricated using a process that consisted of three general steps: (i) photolithography on a Whatman filter paper 1 using SU-8 photoresist, according to product specifications (MicroChem Corp., Newton, Mass.); (ii) fabrication and attachment of metal-tape wires: 50 nm layer of gold was sputtered (Cressington Model 208HR sputter coater, 60 mA, 50 s sputtering time) onto a matt side of the Scotch tape and attached to the device as a 1-mm-wide strip; and (iii) assembling all the layers of the device.

Switching the Channels On/Off

To investigate the switching on/off process in the paper channel, an aqueous solution of red dye (0.05 mM aq. disodium 6-hydroxy-5-((2-methoxy-5-methyl-4-sulfophenyl)azo)-2-naphthalene-sulfonate, allura red) was used to visualize the effectiveness of the device. The solution was conveyed to the central channel of the device by capillary action. The heating wire was set to 70° C. to stop the flow of the liquid.

Figure 8:
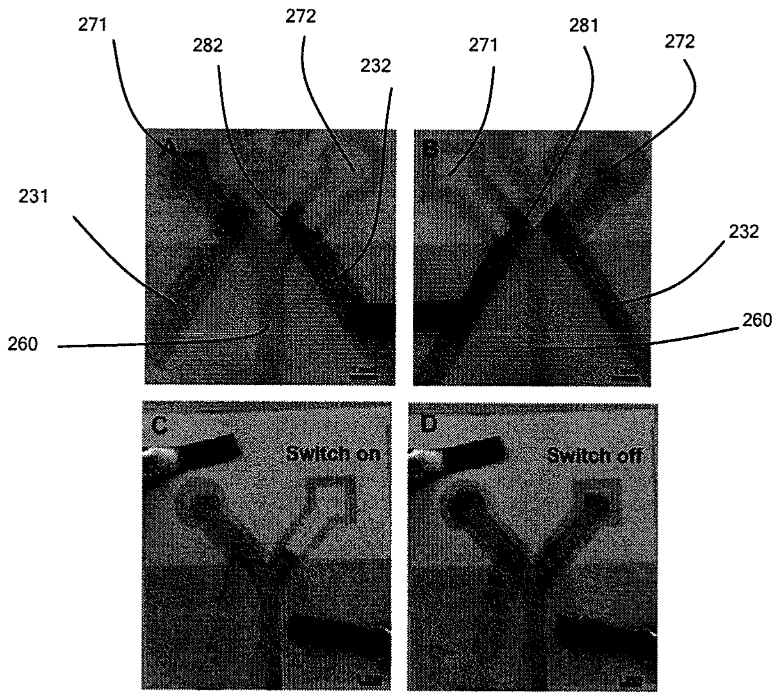
FIG. 8 is a series of representations of photographs of microfluidic devices.

The wires were connected with a tunable current source using alligator clips. The voltage was set to 0.1 V, current 0.037 mA. The device was immersed in the aqueous solution of the dye to about 500 μm deep into the solution to introduce the liquid into the channel by capillary action. To turn off one channel (to close it), the current that was passing through the wire across that channel was adjusted to give about 80° C. (the temperature was measured with IR thermometer), while the other wire was not turned on (the temperature on that wire was about 30° C.) allowing the liquid to flow (FIG. 8).

When the flow from the central channel was directed to the channel 1, the current on the switch 2 was turned on and the switch 1 was turned off (FIG. 8A). The temperature on the switch 1 was 30° C. The temperature on the switch 2 was 80° C. The cooling time was less than 1 s. The time needed to reach 80° C. was also less than 1 s. When the switch 2 was turned off, the liquid started to flow into that channel (FIG. 8B). The liquid was not entering into the channel 1 since the current on the wire 1 was turned on. The switches 1 and 2 were periodically turned on and off to guide the flow of the liquid. (The liquid was continuously supplied in this experiment). After stopping the flow of the liquid in channel 2 (FIG. 8C), the switch 2 was turned off and the liquid could flow further into the channel (FIG. 8D).

Simultaneous Control of the Flow of the Liquid in Multiple Channels

Figures 10A, 10B:
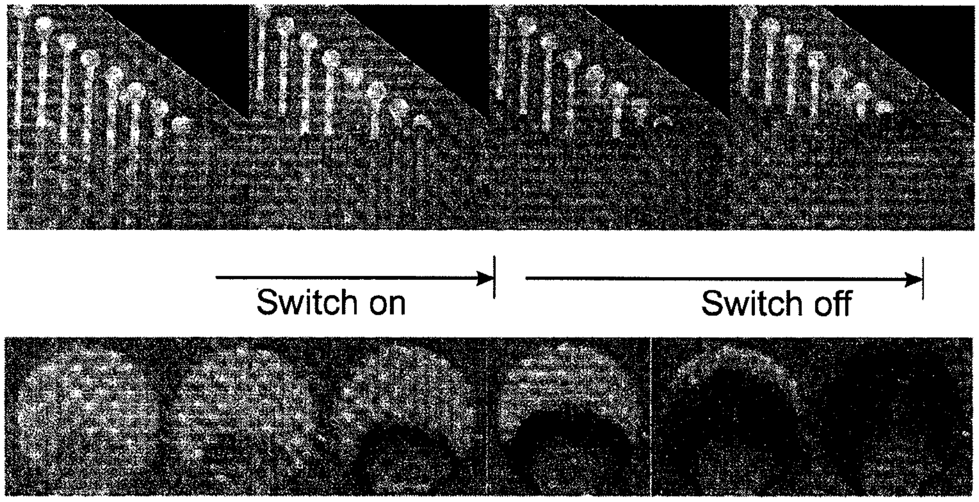
FIG. 10A depicts the set of channels with an applied wave-shape wire across the device.
FIG. 10B depicts an enlargement of channel nr 8 from FIG. 10A.

Single metal-tape hybrid wire was attached across the set of multiple channels in order to stop the liquid at different length of those channels. The wire was positioned in the manner so the switch was placed at a different part of each channel. In this particular experiment, a conductive pen was used to draw the wire (just to simplify the process but the same approach could be conducted using a metal-tape hybrid wire). The wire was drawn on the transparent tape attached to the paper device (FIG. 10). To visualize the flow of the liquid, blue or yellow dye [0.05 mM aq. erioglaucine (ammonium, ethyl(4-(p-(ethyl(m-sulfobenzyl)amino)-alpha-(o-sulfophenyl)benzylidene)-2,5-cyclohexadien-1-ylidene) (m-sulfobenzyl)-, hydroxide, inner salt, disodium salt) and 0.05 mM aq. tartrazine (4,5-dihydro-5-oxo-1-(4-sulophenyl)-4-[(4-sulfophenyl)azo]-1H-pyrazole-3-carboxylic acid trisodium salt), respectively] was added to MilliQ water. The colored liquid was delivered to the device by immersion of channel(s) into the solution. In a first experiment (FIG. 10), an aqueous solution of blue dye was introduced to the channels and the liquid was stopped by the round/curved wire that was crossing 8 out of 16 channels (FIGS. 10A and 10B). The wire was heated up to 70° C. in order to stop the flow of the liquid. Half of the channels were serving as a reference to follow the flow of the liquid without heating. When the heating was off, the liquid passed through the channel until it filled it up completely.

Subsequently another dye (yellow dye) was introduced to the same device, and the solution was stopped where the wire was attached (FIGS. 10C and 10D). Multiple components can be injected to the system which can be useful in, for example, the synthesis on the chip.

In a second experiment, a wave-shape wire was drawn across channels using conductive pen (FIG. 11A). The wire was heated up to 70° C. The flow of the liquid was stopped along various lengths of the channels, in the place were the wire was crossing. In places where the wire was very close to the end of the channel, a high concentration of the dye was observed (FIG. 11B) while at the position where the wire was far from the end of the channel dilution process accrued.

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. An assay device comprising a porous, hydrophilic substrate having first and second faces, a fluid-impermeable barrier permeating the thickness of the substrate and defining a boundary of an assay region and a boundary of a channel region fluidically connected to the assay region, an electrically conductive material disposed on one of the first and second faces of the substrate and spanning the channel region in proximity to said assay region, a detection reagent disposed in the assay region, and an insulating material disposed between the conductive material and the substrate.

2. The device of claim 1 wherein the electrically conductive material is a metal or conductive polymer.

3. The device of claim 2 wherein the metal is Sn, Zn, Au, Ag, Ni, Pt, Pd, Al, In, or Cu.

4. The device of claim 1 wherein the barrier defines a plurality of assay regions and a plurality of channel regions, and the device comprises one or more strips of conductive material spanning one or more said channel regions.

5. The device of claim 1 wherein the channel region is in fluid communication with a sample deposition region and provides a fluidic pathway within the substrate between the sample deposition region and the assay region.

6. The device of claim 1 comprising a pattern of said barriers comprising a photoresist or a curable polymer.

7. The device of claim 1 comprising a substrate comprising nitrocellulose acetate, cellulose acetate, cellulosic paper, filter paper, tissue paper, writing paper, paper towel, cloth, or porous polymer film.

8. The device of claim 1 wherein the conductive material comprises a strip.

9. The device of claim 1 further comprising an electric current source connected to the conductive material for inducing resistive heating therein.

10. The device of claim 9 wherein the conductive material has a resistance of about 20Ω to about 500Ω.

11. The device of claim 1 wherein the conductive material functions as a valve to modulate flow of fluid through said channel region.

12. The device of claim 1 further comprising an integrated circuit, resistor, capacitor, transistor, diode, or a mechanical switch attached to the channel region or to the conductive material.

13. The device of claim 1 wherein the detection reagent responds to the presence of an analyte to produce a signal visible to the naked eye.

14. The device of claim 1 wherein said conductive material is adapted for pumping a fluid, evaporating a fluid, concentrating an analyte by evaporation, controlling the direction of flow of a fluid, turning on/off a flow of a fluid, sensing temperature of a fluid in said substrate, heating a fluid for reaction or incubation of cells, cooling a fluid in said substrate, temperature cycling for executing PCR in said substrate, concentrating a magnetic field in said substrate, applying a magnetic field for separations, capturing particles or analytes, or applying an electrical or magnetic field in said substrate for mixing.

15. A method of performing an assay comprising providing an assay device of claim 1, applying an electric current to the conductive material, contacting the channel region with a fluid sample, and observing a visually detectable signal in the assay region.

16. A method of controlling the movement of a fluid sample through an assay device, the method comprising providing the assay device of claim 1, contacting the channel region with a fluid sample, and applying an electric current to the conductive material thereby to modulate fluid flow of the sample in the channel region.

17. The device of claim 7, wherein the electrically conductive material spans the channel region at about 0.5 mm from the assay region.

18. The device of claim 17, wherein the device is configured so that heating the channel region in proximity to the electrically conductive material to a temperature greater than 60° C. prevents water from wicking through the channel past the electrically conductive material.

19. The device of claim 18, wherein the device is configured so a portion of the channel heated to 65-75° C. cools to 23° C. in less than five seconds upon termination of electrical current to the electrically conductive material.

20. The device of claim 17, wherein the electrically conductive material is a gold wire, and the insulating material is tape.

* * * * *